United States Patent
Papier et al.

(10) Patent No.: US 8,538,770 B2
(45) Date of Patent: Sep. 17, 2013

(54) SYSTEM AND METHOD TO AID DIAGNOSES USING CROSS-REFERENCED KNOWLEDGE AND IMAGE DATABASES

(75) Inventors: Arthur Papier, Rochester, NY (US); Nancy P. Weyl, Churchville, NY (US)

(73) Assignee: Logical Images, Inc., Rochester, NY (US)

( * ) Notice: Subject to any disclaimer, the term of this patent is extended or adjusted under 35 U.S.C. 154(b) by 3457 days.

(21) Appl. No.: 09/919,275

(22) Filed: Jul. 31, 2001

(65) Prior Publication Data
US 2002/0021828 A1 Feb. 21, 2002

Related U.S. Application Data

(60) Provisional application No. 60/222,573, filed on Aug. 1, 2000, provisional application No. 60/275,282, filed on Mar. 13, 2001.

(51) Int. Cl.
*G06F 17/00* (2006.01)
(52) U.S. Cl.
USPC ............................ 705/2; 128/920; 128/922
(58) Field of Classification Search
USPC .............................................................. 705/2
See application file for complete search history.

(56) References Cited

U.S. PATENT DOCUMENTS

| | | | |
|---|---|---|---|
| 4,130,881 A | 12/1978 | Haessler et al. | |
| 4,731,725 A | 3/1988 | Suto et al. | |
| 4,945,476 A * | 7/1990 | Bodick et al. | 600/301 |
| 5,235,510 A * | 8/1993 | Yamada et al. | 600/300 |
| 5,437,278 A * | 8/1995 | Wilk | 600/425 |
| 5,605,153 A | 2/1997 | Fujioka et al. | |
| 5,878,746 A * | 3/1999 | Lemelson et al. | 600/407 |
| 6,014,451 A * | 1/2000 | Berry et al. | 382/110 |
| 6,021,404 A * | 2/2000 | Moukheibir | 706/46 |
| 6,032,120 A | 2/2000 | Rock et al. | |
| 6,108,635 A * | 8/2000 | Herren et al. | 705/2 |
| 6,132,218 A | 10/2000 | Benja-Athon | |
| 6,149,585 A | 11/2000 | Gray | |
| 6,260,021 B1 | 7/2001 | Wong et al. | |
| 6,272,469 B1 | 8/2001 | Koritzinsky et al. | |
| 6,292,577 B1 * | 9/2001 | Takahashi | 382/128 |
| 6,353,817 B1 * | 3/2002 | Jacobs et al. | 706/50 |
| 6,424,973 B1 * | 7/2002 | Baclawski | 707/102 |
| 6,491,651 B1 * | 12/2002 | Leahy et al. | 601/40 |
| 2002/0052763 A1 * | 5/2002 | Jung Richardson | 705/3 |
| 2003/0036683 A1 * | 2/2003 | Kehr et al. | 600/300 |

* cited by examiner

*Primary Examiner* — Calvin L Hewitt, II
*Assistant Examiner* — John M Winter
(74) *Attorney, Agent, or Firm* — Duane C. Basch; Basch & Nickerson LLP

(57) ABSTRACT

The present invention is a method and apparatus for increasing the usefulness of visual knowledge in a number of applications. It distills the relationships between characteristics and hypotheses into database form, thereby organizing visual information in a manner suitable to aid the user in the investigation of the various hypotheses (medical diagnosis, pill identification, plant/animal identification, cause of death, cause of accident, etc.). The invention sidesteps unresolved issues around knowledge engineering by not automating a decision making process. Rather, the present invention utilizes a relational database to dynamically respond to textual and visual findings as an aid to assist a user reaching a reasoned conclusion based upon information available by direct observation and comparison with stored image and textual data.

30 Claims, 16 Drawing Sheets

SYSTEM AND METHOD TO AID DIAGNOSES USING CROSS-REFERENCED KNOWLEDGE AND IMAGE DATABASES

CROSS REFERENCE

Priority is claimed from the following related Provisional Applications, which are hereby incorporated by reference for their teachings:

"SYSTEM AND METHOD TO AID DIAGNOSES USING CROSS-REFERENCED KNOWLEDGE AND IMAGE DATABASES," Nancy Weyl, Application No. 60/275,282, filed Mar. 13, 2001;

"SYSTEM AND METHOD FOR CROSS-REFERENCED KNOWLEDGE AND IMAGE DATABASES TO REDUCE DIAGNOSTIC UNCERTAINTY," Arthur Papier, Application No. 60/222,573, filed Aug. 1, 2000; and "PILL IDENTIFICATION PERIPHERAL," John A. Weyl, Application No. 60/307,919, filed Jul. 26, 2001.

This invention relates generally to a system and method for aiding diagnoses, and more particularly to a cross-referenced knowledge and image database wherein an image-centered database is cross-referenced with textual database information to support the investigation of diagnostic hypotheses and to narrow and create at least one subset of possible diagnoses.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND AND SUMMARY OF THE INVENTION

The present invention is a system and method for automatically controlling the selection and display of visual information to assist a user in testing and/or arriving at diagnostic hypotheses. One embodiment of the invention may be employed as a visual medical browser, and is more particularly referred to herein as a visual diagnostic system (VisualDx™). The VisualDx system is intended for use in patient treatment or care settings to assist users in identifying possible diagnoses based upon a set or constellation of patient findings.

Although portions of the following description will focus on a particular dermatological application for aspects of the invention (Adult Dermatology), it should be further appreciated, that various alternative applications for the underlying system and components are possible. One such alternative application is a system (e.g., emergency medicine) that assists in the identification of pills or other oral medications that a patient might present during treatment. A similar pill-identification application could be one where law enforcement technicians use the system as a first line of identifying narcotics or other oral medications seized during an arrest or investigation.

The present invention is intended to be an improvement to paper-based atlases that doctors consult when investigating possible diagnoses. Similar, visual and textual information is presented to users using a computer-driven interface that not only speeds access to the information, but can also assist the user in the diagnostic process by focusing on relevant categories or constellations of findings most indicative of the diagnoses. The system is believed to be distinguishable from other medical diagnostic system that simply seek a set of symptoms and input the symptoms to an artificial-intelligence engine to create a ranked (by probability) list of diagnoses. To the contrary, the present invention uses categories or constellations of patient findings, or sample characteristics, to provide a combination of textual and graphic/image information to the user, so that the user may test or review a plurality of possible diagnoses without being "lead" to one diagnosis over another. In other words, the present system provides a source of knowledge (medical or other), in multiple forms, that allow users to test diagnostic hypotheses against an image database using patient findings or sample characteristics.

In the visually centered medical specialties (e.g., dermatology, radiology, ophthalmology, pathology) physicians hone their ability to classify, correctly identify, and relate the visual features of disease to a knowledge base of diagnostic features, criteria etc. Accordingly, an objective of the instant invention is a software-based schema or strategy to assist less experienced medical users in the interpretation of visual clues (presentations and/or findings) as they relate to diagnostic hypotheses. Both graphical representations, drawings and refined picture icons (PICONS) are used to augment the medical keywords in the software database.

One purpose of the present invention is to provide near instantaneous access to diagnostically relevant images at the place where they may be used—for example when interviewing a patient. The present system relies upon a combinatorial, non-expert system approach to diagnosis or identification along with access to related images. Images, whether found under a microscope, on a radiological view box or a computer monitor, are often signs or indicators for diagnoses and diseases. Users of medical diagnostic aspects of the present invention are intended to be health-care personnel who need real-time access to data at the point of patient care (e.g., outpatient offices, emergency departments, walk-in clinics, hospitals, military medical facilities, occupational clinics, long-term care facilities, and telemedicine departments). However, the invention may also be used in educational or reference-based environments.

The present invention, to a significant degree, builds upon an innate human ability to match patterns. This is the basis for any pictorial handbook or guide, such as in field guides for plants, birds, animals and atlases in medicine. Moreover, all visual identification problems benefit from user experience and knowledge. When prior visual knowledge is limited, picture or image "centered" reference materials can assist the inexperienced. Paper based, pictorial references have a linear structure and do not allow for user-defined groupings and matching of pictures. Software based image systems offer the possibility of combinatorial searching as well as user-defined comparison of possibilities.

The visual diagnostic embodiment of the present invention, VisualDx, assembles textual and visual knowledge, thereby creating the ability to "presort" and display images so that a user can more effectively engage in pattern matching. These unique functional, organizational and graphical display capabilities are useful within any professional area where an individual has to make a visual "diagnosis" or identification, or recognize a visual feature.

It is believed that aspects of the present invention have particular relevance within traditional medicine and health-care industries, including but not limited to:

Dermatology
Dermatopathology
Ophthalmology

Dentistry
Pathology including all subspecialties, Hematology, renal, neuropathology, etc.
Obstetrics/Gynecology
Otolaryngology
Gastreneterology (Endoscopic images)
Surgery (intraoperative images)
Urology (Endoscopic images)
Pulmonary Medicine (Endoscopic images)
Microbiology (cultures, microscopic slides, e.g. gram stains)
Oral Medicine
Patient self-use (diagnose your own rash or child's diaper rash)

In accordance with the present invention, there is provided a system to aid in a visual diagnostic process, comprising: an image database; a knowledge database, cross-referenced to said image database, for the purpose of assisting in the diagnostic process; a user-interface to solicit, from a user, a plurality of descriptive characteristics of a sample requiring diagnoses; a diagnostic engine, responsive to said characteristics, wherein said characteristics of the sample are employed by said engine to identify, from a plurality of possible diagnoses, a subset of diagnoses that are consistent with the characteristics; and using the subset of diagnoses, reorganizing an information space of said image database for concurrent presentation of a plurality of images for user review via the user-interface.

In accordance with another aspect of the present invention, there is provided a method for aiding a visual diagnostic process, including the steps of: creating an image database from a collection of images pertaining to a particular subject matter; creating a knowledge database with other data related to the particular subject matter, wherein said knowledge database is cross-referenced to said image database, for the purpose of assisting in the diagnostic process; collecting from a user, through a user-interface adapted to the particular subject matter, a plurality of descriptive characteristics of a sample requiring diagnoses; in response to said descriptive characteristics, identifying, from a plurality of possible diagnoses included within the knowledge database, a subset of diagnoses consistent with the descriptive characteristics collected from the user; and using the subset of diagnoses, reorganizing an information space of said image database for concurrent presentation of a plurality of images related to the descriptive characteristics for user review via the user-interface.

One aspect of the invention is based on the discovery that general and primary care physicians are often ill-informed or lack sufficient tools and resources to investigate a plurality or alternative diagnostic hypotheses. This discovery addresses problems that arise in traditional patient diagnostic situations, where a medical practitioner is faced with first identifying a set of possible diagnoses based on symptomatic and other patient findings, and then working to select at least one particular diagnosis for treatment.

This aspect is further based on the discovery of techniques that can appropriately match relevant visual information to unique characteristics of the individual patient presentation or sample being analyzed. A purpose of the various embodiments of the present invention is to provide near instantaneous access to relevant images at or near the place of use of such information. For example, identification of a street drug would be useful to both police investigators at a crime scene or crime lab, as well as to emergency room personnel. Similarly, coroners may be able to employ the present system in assisting with a determination of the cause of death, perhaps even in close proximity to an examination area, where comparisons of actual specimens/samples could be made to the images cataloged in the system. The present system uses a combinatorial, non-expert approach for identification/diagnosis and access to images. Visual characteristics or clues, wherever found, are often signs or indicators for identification and/or diagnosis. Time-critical access to relevant visual clues can be achieved when related findings or characteristics are correlated to profiles, then images are preferably displayed as "stacks" or "clusters" within the context of the inputted findings or characteristics. The display of relevant images in relation to various diagnoses, or as a stack of images related to a particular diagnosis, allows a practitioner to visually compare and contrast the images with their own observations of the patient, thereby improving the likelihood of an accurate and timely diagnosis.

The objectives of the present invention include: the creation of a streamlined process for acquiring and tracking images to assist in diagnosis and identification; to reference all items in a knowledge base to the associated descriptive literature; to implement a user-friendly, efficient and network distributed data entry/access system; to capitalize on network connectivity for integrating knowledge sources; to publish images on transportable media and over network connections for public and private use; to create focused subset modules of the knowledge base to serve critical areas of need for identification and diagnostic information (e.g. adult dermatology, fever and rash, pill identification, plant identification, etc.).

An aspect of the invention is based on the fact that professionals lack sufficient tools and resources to investigate a plurality of alternatives when seeking to identify a specimen or verify a diagnostic hypothesis. This discovery addresses problems that arise in traditional situations, where a professional (doctor, nurse-practitioner, coroner, police investigator, etc.) is faced with first reducing the set of possible identifications or diagnoses to a number with which the professional can work based upon a set of predetermined characteristics and findings, and then working to complete the identification or diagnosis.

One aspect of the present invention is generally referred to as a visual browser and the system is intended for use as a tool to assist in the identification of particular traits or common visual manifestations and their association with data in particular fields of investigation (e.g., medicine, drug enforcement, etc.). The various embodiments of the present invention are intended to be improvements over paper-based atlases and incomplete or non-existent databases that doctors and other professionals consult when attempting to identify a physical element or investigating hypotheses (e.g., diagnoses). Throughout all of the various embodiments, similar, visual and textual information is presented to users using a computer-driven interface that speeds access to the information, and can also assist in the diagnostic/identification process by focusing a user on relevant characteristic categories or constellations of findings having a likelihood of leading to a conclusion (e.g., identification, confirming a diagnoses, estimation of damage, etc.).

The techniques described herein are advantageous because they can be adapted to any of a number of diagnostic situations, where a practitioner/user is faced with making a diagnosis, or similarly testing a plurality of diagnostic hypotheses. As a result of the invention a practitioner faced with such a situation is aided by image/graphic and textual tools that allow them to consider a range of possible diagnoses and to review details of each.

Figure 1:
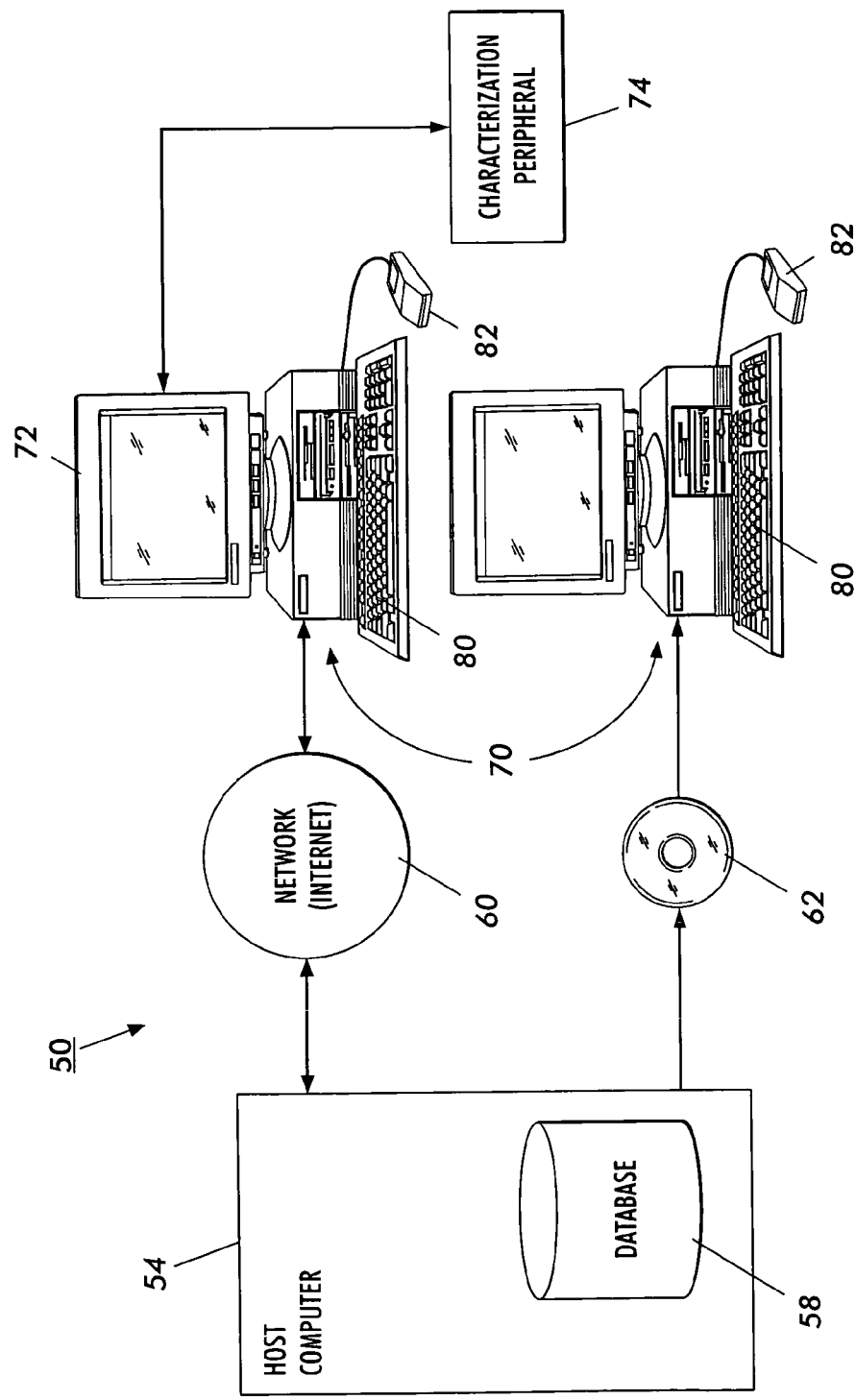
FIG. 1 is an exemplary block-diagram depicting an embodiment of a system in which the present invention might operate.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENT

For a general understanding of the present invention, reference is made to the drawings. In the drawings, like reference numerals have been used throughout to designate identical elements. In describing the present invention, the following term(s) have been used in the description.

"User input circuitry" is circuitry for providing signals based on actions of a user. User input circuitry can receive signals from one or more "user input devices" that provide signals based on actions of a user, such as a keyboard or a mouse. The set of signals provided by user input circuitry can therefore include data indicating mouse operation and data indicating keyboard operation. Signals from user input circuitry may include a "request" for an operation, in which case a system may perform the requested operation in response.

An "image" is a pattern of physical light. A "display" is an image output device that provides information in a visible form. A display may, for example, include a cathode ray tube operatively driven by a computer operatively connected to it; an array of light emitting, reflecting, or absorbing elements; a structure that presents marks on paper or another medium; or any other structure capable of defining an image in a visible form. To "present an image" on a display is to operate or drive the display so that a viewer can perceive the image.

A wide variety of display techniques for data processing systems are available including, for example, various graphical user interfaces, but, despite their diversity, these techniques tend to have certain common characteristics. One fundamental common characteristic is that a display produces human perceptions. In this application, the term "display feature" refers to any human perception produced by a display.

A "display object" or "object" is a display feature that is perceptible as a coherent unity. An "object surface" or "surface" is a display feature that is perceptible as a surface of a display object; for example, the outer boundary of a three-dimensional display object is a surface. A "region" on a surface is a bounded area of the surface; for example, a single point is the smallest possible region of any surface. A "shape" is a display object that has a distinguishable outline; for example, a circular display object is a shape.

A "structure" is a display feature that includes other display features within it, all of which appear to be connected into a unitary element of the display or user-interface depicted thereon.

A "selectable unit" is a display feature that is perceived as a bounded display area that can be selected. For example, any of the textual links displayed in region 288 of the interface screen in FIG. 6. The term "select," when used in relation to a selectable unit, means a user input operation that includes a signal from user input circuitry that uniquely indicates the selectable unit. The user can, for example, use a pointing device such as a mouse to select a selectable unit by indicating its position via a cursor on the display and clicking a button on the pointing device. In general, a selectable unit may take any appearance, and is not limited to a visually distinguishable feature or set of features that appears to be a coherent unity.

A "finding" is factual data about a patient or characteristic associated with a diagnosis. There are two basic categories for findings. Findings that can be described efficiently with words alone are called textual findings, whereas findings that can be described most efficiently with icons or illustrations are called visual findings.

Turning now to the substantive description of the elements, features and functions of the present invention, the following description is divided into multiple sections, each intended to highlight and describe in detail a particular aspect of the system and/or methods employed in implementing an embodiment of the invention. While the description will focus on the use of the system and method for the diagnosis of adult diseases having a dermatological manifestation of symptoms (e.g., VisualDx: Adult Dermatology), it is understood that similar techniques might be employed for the identification of oral medications such as pills (tablets, capsules, etc.), or the various critical areas of need for medical information indicated previously. Accordingly, the following description will first present the system requirements and architecture for preferred and alternative embodiments, and will then discuss the use of the invention in accordance with an the VisualDx system.

I. System Requirements

Referring to FIG. 1 there is depicted a representative embodiment of the present invention. The present invention will operate in two configurations: as a network-based client/server application targeted toward medium to large institutional customers: and as a single user product with both client and server components residing on the same computer. However, these configurations may be implemented with the same software base. In particular, the present invention may be implemented in association with a networked or distributed computer system 50. Such a system preferably includes a host computer 54 having a mass-storage device operatively associated therewith for retaining a master database 58.

The data and operating software components of the system may be distributed to one or more remote computers 70 via a network connection 60 (e.g., Internet) or via removable media such as a compact disk 62. Although various alternative system configurations are possible, the computer system 70 preferably includes a color monitor or display 72 capable of displaying image information at a suitable resolution, for example, a 1024×768 pixel resolution using 16-bit color (65536 colors). System 70 further includes a system unit (desktop, tower or mini-tower configuration) having a Pentium II® processor (Intel Corporation) or an equivalent thereof operating at 233 MHz or higher. The system unit should further include a CD-ROM drive for installation of the software, a hard drive or similar mass storage device and at least 32 Megabytes of RAM (not shown) in order to operate the software. In a preferred configuration the software is run on a system employing a Microsoft Windows based operating system—preferably Windows 95 or higher and Java or Macromedia Director. However, it is further contemplated that the functionality of the system may be further implemented and enhanced using a compatible browser interface (e.g., Windows Explorer, Netscape Navigator).

System 70 also preferably includes one or more user input circuitry devices that enable a user to interactively operate the software. Examples of suitable devices include keyboard 80 and mouse 82, as well as other devices such as wireless communications tools (e.g., Palm Pilot and remote controls using infrared links). As will be described below in more detail, the software operating on the remote computers preferably depicts various objects and selectable display units for selection by the user in order to characterize the patient, sample or other object of the diagnosis. It will also be appreciated that the diagnosis, or characterization, may be complemented by the use of a standard characterization device, 74 which is depicted in the figure as a characterization peripheral. Such a device may be an imaging device in one embodiment of the invention (e.g., pill identification), or it may be a testing device in still another embodiment, where the output of the device is suitable for providing one or more characteristics of a sample obtained under standard conditions. Such a system is further described in U.S. Provisional Application for a "PILL IDENTIFICATION PERIPHERAL," by John A. Weyl, filed Jul. 26, 2001, hereby incorporated by reference for its teachings. Based upon the constellation of findings or characteristics indicated by the user, both as input by the user or directly provided by the characterization peripheral, a subset of possible diagnoses or identifications is selected from the database for presentation and further consideration by the user—where the presentation preferably includes at least one reduced-size or thumbnail image depicting an example of the diagnosis (e.g., skin lesion picture, pill picture).

Although system 50 may be a stand-alone system, it is entirely possible to install and operate the present invention in a network (LAN, WAN or Internet) environment, wherein one or more users may have access to independent "views" of the system at any particular time. In such a system it is anticipated that the software would be installed on a server in a client/server system, so that the plurality of users may access and use the software concurrently. It is further contemplated that system 50 may be implemented or hosted using an application service provider (ASP) wherein a user would access the system via a subscription or similar business relationship.

In a further alternative embodiment, it is contemplated that the Adult Dermatology module included as the detailed example herein is only one of many such modules, some of which may be interrelated. Alternative modules include, but are not limited to, pediatrics (including pediatric dermatology), geriatrics, genetics, occupational medicine, human immunodeficiency virus (HIV), birthmarks, wound care, infectious diseases, diabetes, environmental exposures, body-region specific modules, forensic medicine, plant identification, poisonous plant identification, and poisonous snake identification. A user might access one or more of such modules through an upper-level menu or set of icons that are not shown. Moreover, the menu contents or icons may be displayed as a function of those modules for which the user and/or the user's practice, organization or company has subscribed. In the multiple-module environment, it is further contemplated that the modules and subscription offerings may be delivered through an application service provider (ASP) approach via the Internet or equivalent wide-area network from a common host location (possibly including mirror or redundant sites to assure access). Each of the modules would, to the extent possible, employ a similar user-interface "look and feel" in order to assure that a user familiar with the operation of one module will quickly become adept with using other modules. In other words, the user-interface will remain the same and the user options, selections and data would change based upon the module and the most relevant information necessary to conduct a search for possible diagnoses. Moreover, the sum of the plurality of modules, when exhaustively developed, would ultimately result in a "complete" listing of possible diagnostic categories or constellation of findings for particular medical technologies (dermatology, radiology, etc.) or sample types (pills, plants, etc.).

Figure 2:
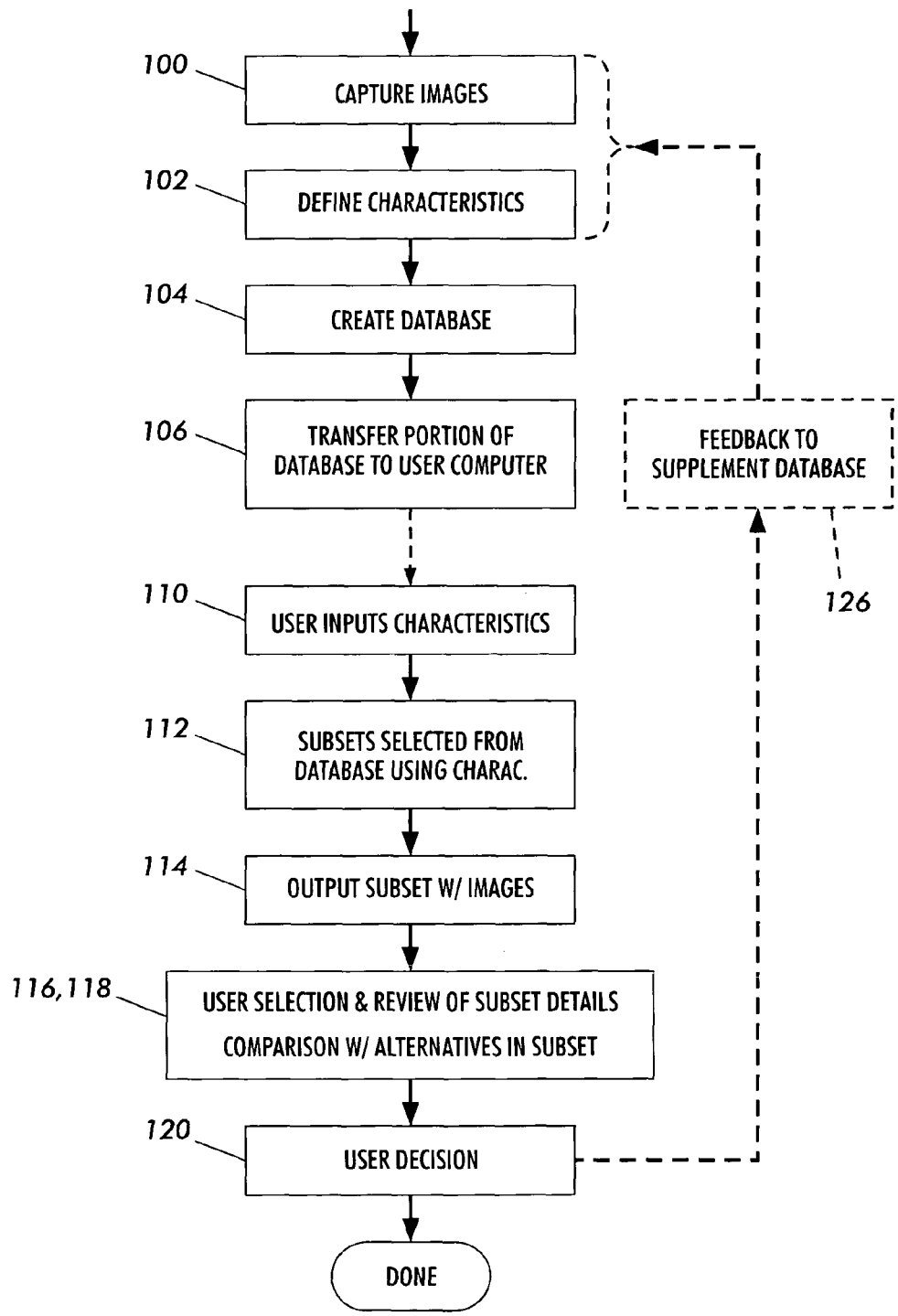
FIG. 2 is a flowchart depicting the general steps in the creation and use of an embodiment of the present invention.

Referring next to FIG. 2, system 50 operates in accordance with the general steps depicted in the flowchart. More specifically, starting with step 100, the images to be used in the system are captured or identified from existing digital images, either obtained directly using digital photography or via the digitization of existing photographs using well-known scanning technologies. It will be appreciated that various methods may be employed to capture such pictures as are well known in the art of digital imaging and digital photography. In one embodiment, each digital image shall be available in at least two, and preferably three, sizes (pixel width×pixel height): 900×675, 384×288, and 160×120 pixels. In addition to images, the database 58 of the present invention includes characteristics of the item (e.g., disease, pill, etc.) that is the subject of the image as described in more detail with respect to the database of FIGS. 3 and 4. Database 58 is preferably a relational database that supports structured query language (SQL) queries using open database connectivity (ODBC). Step 102 represents a corresponding entry of characteristic information related to the image.

As will be described below with reference to the database architecture, the image and characteristic information is embodied in a plurality of relational tables within the database that is created at step 104. Once the database has been created, it is available for distribution or transfer to a user's computer as indicated by step 106.

Following the transfer or download of the database and associated integration software that is executed to administer the user's use of the system, the VisualDx software is started and the user, working for example on a remote computer 70 as depicted in FIG. 1, may input one or more characteristics that are observable about the patient or sample (e.g., type of skin lesion, shape of pill) at step 110. Based upon the characteristic(s) input by a user, the system then automatically analyzes the user input, at step 112, and automatically selects one or more related diagnoses contained within the database, where the selections include at least one of the identified characteristics. Output to the user, for review, is accomplished at step 114, and preferably includes pictorial representation of the diagnoses subset identified via the database.

Subsequently, the user, as indicated by steps 116 and 118, may select one or more of the diagnoses in the subset for review, including review of one or more images associated with a particular diagnosis, and review of textual information pertaining to the diagnosis. Moreover, as indicated by step 118, the user interface described in detail below permits the user to compare and contrast alternative diagnoses within a subset so as to improve the likelihood of an accurate diagnosis by the user. Lastly the user may complete the diagnostic or identification process by making a decision as reflected in step 120.

It is further contemplated that, in some implementations of the present invention, the diagnosis and related text and image data may be fed back to the host computer for inclusion in subsequent releases of the database. In this way, the system may improve the rate at which new diseases, street drugs, etc. are identified and completely characterized for addition to the database.

II. Database/Knowledgebase Architecture

In one embodiment, the VisualDx software includes a Diagnostic Module as a subcomponent aimed at finding a set of diagnoses that match, or partially match, user entered information (textual and visual findings). Diagnostic modules preferably have a theme (e.g. General Adult Dermatology, or Drug Eruptions and Reactions). Moreover, VisualDx also includes an Image Atlas Module subcomponent whose function is to find a set of images that match or partially match some user-entered information (keywords, diagnosis, etc.).

Figure 3:
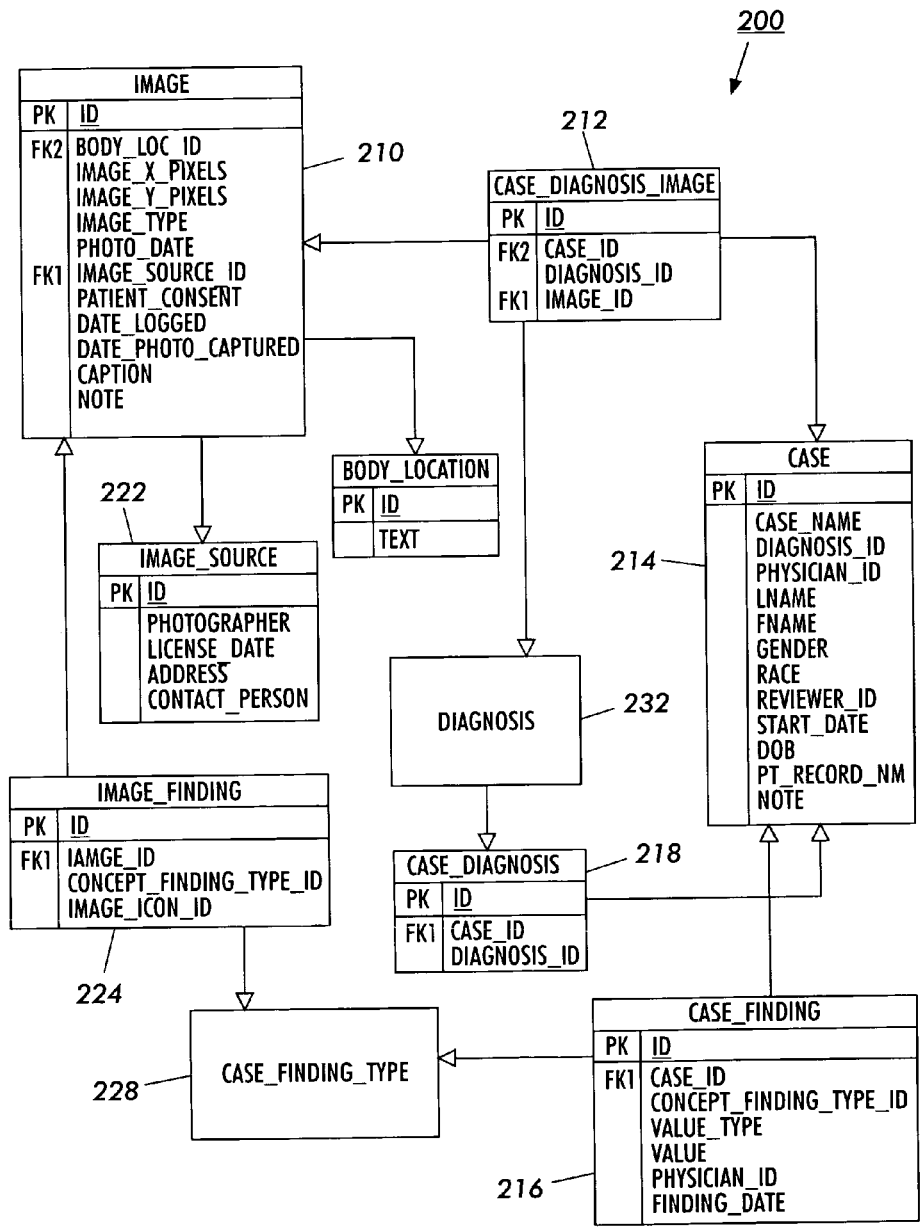
FIGS. 3-4 are illustrative examples of a database schema that may be employed in implementing an embodiment of the present invention.
Figure 4:
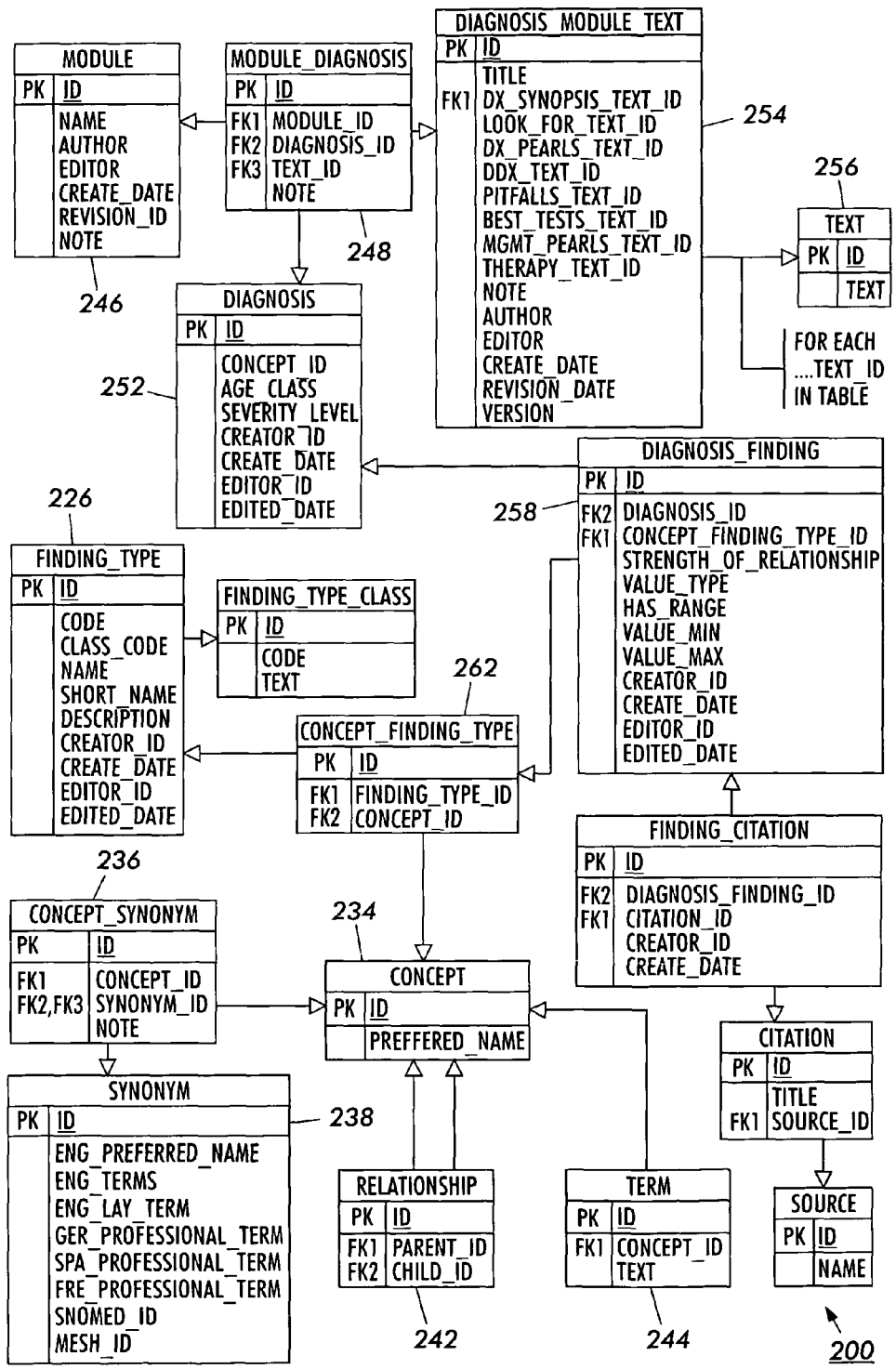

As implemented in accordance with aspects of the present invention, the knowledge database, or knowledge base, is a relational database wherein the various database tables in schema 200 of FIGS. 3 and 4 are employed as the basis of any diagnoses presented by the system.

The knowledge base 200 is preferably comprised of a plurality of relational tables that represent icons, text and images employed by the diagnostic engine and associated user-interface. As will be described below, a user may select visual and textual characteristics or findings without prior knowledge of the specialized vocabulary associated with those findings, and the selections, via knowledge base 200, will be translated into queries and output containing findings, diagnoses, images, and their relationships to each other. Knowledge base schema 200 is preferably optimized in a manner that significantly reduces the size of the database. In light of the ever-increasing speed of computers, this alternative schema was developed so as to reduce the size of the database, thereby improving the delivery capability, albeit possibly compromising speed unless a faster processor is employed to operate the software.

The relationships between the tables are indicated by the lines therebetween. Moreover the PK index, having values FK1, FK2 and FK3, represent foreign keys to related tables.

In order to generally characterize the functionality built into the knowledgebase 200 through the various objects and their interrelationships, the following brief descriptions of the tables are included:

Image Table 210: each of the Image records represented via table 210 contain image characteristics, one or more of which may not be available to a user of the system (e.g., PATIENT_CONSENT). For example, the CAPTION field represents the caption that will be assigned to the image to be viewed by the end user.

Case_Diagnosis_Image Table 212: this table links together a case, its images and the diagnoses. A case can have multiple images and diagnoses.

Case Table 214: The Case record represents a particular patient with associated defining characteristics found in related tables, Case_Finding table 216 and Case_Diagnosis table 218. There is a particular set of images associated with each case. There are also findings, e.g. the patient's symptoms, lab values, etc that are associated with the case, and which may be employed as supplemental characteristics to be considered relative to a diagnosis.

Image_Source Table 222: Image source records contain all information about the source of the image, the photographer, license to image so as to assure that the system is able to employ only those images approved for use.

Image_Finding Table 224: Links together an image with its inherent morphologic characteristics. The Image is assigned morphologies by the expert reviewer. In this table the image is linked to these morphologies (the morphologies are concepts, the concepts are assigned a finding type in the Finding_Type table 226; e.g. lesion type (vesicle, pustule etc., configuration, distribution, dysmorphology). In the preferred embodiment, an image can have multiple morphologies.

Case_Finding Table 228: Links the specific patient findings to the case record. (e.g. the actual patient's symptoms, signs, etc.)

Case_Diagnosis Table 218: Links the diagnoses 232 to any given case. A patient (case) can have multiple, co-occurring, diagnoses.

Concept Table 234: Concepts are essential entities. They are unique, discrete and non-redundant. Every entity in the database is a concept. Concepts are contextualized in terms of where they fit in a web structure. They can have parents and children. The parent-child relationship allows for the placing of diagnoses and findings within logical knowledge hierarchies. For instance, inguinal lymphadenoapthy (swollen lymph nodes in the groin area) are a subtype of lymphadenoapthy, which is a more general statement; swollen lymph nodes are occurring, but a particular location is not specified. The end user may want to be specific and say that just the groin lymph nodes are swollen, or alternatively, the user may want to say all lymph nodes are swollen. The system must account with precision for either scenario. Most symptoms, signs, diagnoses, fall within such a hierarchical structure. In the case of both diagnoses and findings, such a knowledge structure allows for the end user to search the specific or general, and retrieve broader or more limited search results (inguinal lymphadenopeathy has a more limited set of associated diagnoses in comparison to searching on lymphadenoapthy, which has many more associated diagnoses.)

Concept_Synonym Table 236: this table links concepts to the many synonyms found in the Synonym table 238.

Synonym Table 238: Synonyms can be interface terms for the end user, in professional versions, lay versions, and for foreign language users. This table is a meta-dictionary/thesaurus to enable multiple versions of the end user application without having to recreate a new database to include or accommodate such applications.

Relationship Table 242: Facilitates the creation of a network or "web" of concepts. Diagnoses are situated within a lattice of multiple, parent-child, and child-parent relationships. Allows end-user searching up and down hierarchical trees.

Term Table 244: Facilitates natural language processing of all words within the end user tool and database. In this table concepts are associated with associated terms and synonyms that reflect common terminology and speech. These are terms that are not necessarily included in the synonym table 238 or concept table 234.

Module Table 246: The system allows for multiple problem-oriented modules, each with unique authors, editors. For example, there may be an adult dermatology module and an Ethnic skin diseases module that may have overlapping data. Also, multiple versions of modules can be released over time, meaning that there may be replacement authors, editors etc. The revision Revision_ID field in the table will link to revision details for the modules.

Module_Diagnosis Table 248: Multiple diagnoses are contained within a module. In this table, diagnoses are linked to a module, and texts that are specific to the diagnoses in the module are linked by foreign key as well. In other words, text for a given diagnosis can vary between modules, or even possibly between users in alternative embodiments (e.g., lay or technical terms).

Diagnosis Table 252: Diagnoses are a type of concept. Diagnoses records are listed separately from the concept table as they need to be qualified uniquely for individual modules. As an example the severity of a disease may be context dependent (severity_level), and therefore need to be related to concepts but identified uniquely.

Diagnosis_Module_Text Table 254: Each module has multiple diagnoses, each with their own text seen by the end user. Diagnoses can have differing text depending upon in which module the text appears. For instance herpes simplex in the Ethnic Skin module would have a different "Look for" text than in the Caucasian skin Module, though it is the same diagnosis. The related Text Table (below) serves as a container for multiple versions of texts.

Text Table 256: Text is written to be module specific, but certain shared elements can be "re-purposed" into other modules. The text table contains generic text, available for use in new or alternative modules.

Diagnosis_Finding Table 258: Diagnoses are related to findings, findings such as laboratory values can have a range (value_min and value_max), relationships are entered by the "creator" (CREATOR)ID) and are accordingly reviewed by the "editor" (EDITOR_ID).

Concept_Finding_Type Table 262: Findings can have one or many "finding types". Thus concepts are linked here to the finding type. (For example fever can be a symptom or a sign) in this table the concept is given the finding context.

Finding_Type Table 226: In this table concepts are put into the logical categories of medicine (or for other fields: any specialty domain sensible to the end user). The finding types logically associated with a medial diagnostic system such as VisualDx, include:
Age
Appearance
Exposure
Medical History
Gender Moreover, although not shown in particular, the various images used and displayed by the system are maintained in accordance with an ID field in the Image table 210. The images are preferably stored in a designated location indicated by one or more fields within table 210. The images (not shown in FIGS. 3 or 4) are preferably stored as JPEG files, however any well-known or equivalent image file or image compression format may be used (e.g., TIFF, CPC, PDF, BMP, etc.). In addition, each image preferably has a reduced-size or thumbnail representation (PICON) thereof that may be incorporated with a user-interface display depicting a plurality of such images. It is important to note that, because diagnoses are the output of any query of the knowledge base, the present invention employs images as representations of diagnoses. This is in contrast to the use of an image database where the purpose of a search is solely to locate images having keywords associated therewith.

Referring to FIG. 4, the different types of characteristics or findings depicted in the VisualDx example have complex and rich hierarchies that are preferably expressed with separate database table structures for each type of diagnostic findings. It should be further appreciated that the VisualDx; Adult Dermatology example described herein is but one embodiment for aspects of the present invention and that numerous alternatives exist wherein the cross-referenced knowledge and image databases may be employed to assist with diagnoses or other identifications.

It should be appreciated that alternative database designs may be employed to implemented the present invention. For example, some modules may retain a speed optimized schema (flatter hierarchy) whereas other may use a space-optimized schema; the selection of the schema type being partially dependent upon the module and the needs of the user population.

III. Findings/Characteristics

In the VisualDX embodiment described herein, knowledge base 200 preferably contains tables of medical findings relevant to the diagnoses and images available for browsing. In an alternative embodiment, knowledgebase 200 may include tables of characteristics relevant to the sample to be identified. Users search for diagnoses and their related images by entering their patient's findings through menus of findings. The findings may number in the tens of thousands for a master knowledge base, from which particular modules may be derived, and may be limited to hundreds for a particular problem-oriented module containing a subset of the knowledge base. A module, or subset of the knowledge base, is a particular grouping of diagnoses centered about a visual diagnostic domain or clinical problem area (e.g., adult dermatology).

Due to the large number of findings, users require ways to quickly arrive at a set of possible diagnoses (and associated images for review) using the findings or characteristics available. The possible list of findings is constrained by the number of diagnoses found within a particular module. Visual problem domains represented by each module are, by definition, limited in the number of diagnoses covered and their related findings to be inputted or searched, thus easing user entry of the patient findings. In essence, the limited finding list defines "questions" the medical user would ask a patient for any given module. The complexity of the medical decision-making and the overwhelming cognitive burden imposed by thousands of possible relationships indicates a problem-oriented approach.

Findings may be broadly classified into groupings such as medical history, family history, travel history, age, body location, patient symptoms, visual signs, radiological signs, and so on. In one embodiment, each of these groupings are given their own table structure in the database, thereby optimizing for speed. Alternatively the structure of the database may also be modified so as to replace a flat structure of tables with more levels of indexed findings and diagnostic links as depicted in FIGS. 3 and 4 (more compact structure).

The findings presented in the system are organized, preferably by medical specialists (author and editor in the depicted embodiment), into the smallest sensible unit that can be related to a diagnosis. Different modules of the system need different levels of granularity in their findings. For example, in some fields of medical practice a complex finding such as "blisters less than 3 millimeters in diameter containing yellow fluid" would be the smallest sensible unit. In another field it might make sense to analyze the findings down into "blisters", "less than 3 millimeters in diameter", and "containing yellow fluid."

Some of the granularity problems of findings may be resolved by taking into account the meanings of the parent findings linked to the detailed findings. The parent finding of "blisters containing yellow fluid" might be "fluid filled blister". This holds even more closely to the intent of the present invention of trying to base findings on a one-adjective to one-subject structure. The example above might then look more like:
fluid filled blister
yellow fluid
less than 3 millimeters in diameter The user interface software depicted beginning with FIG. 5 would keep track of this semantic linking, keeping the parent finding information in view as part of the total information associated with a set or findings. In other words, using one or more tables in the database, and linked tables associated therewith, the user-interface would continually update the findings as well as selected or possible diagnoses associated with a particular patient.

Figure 5:
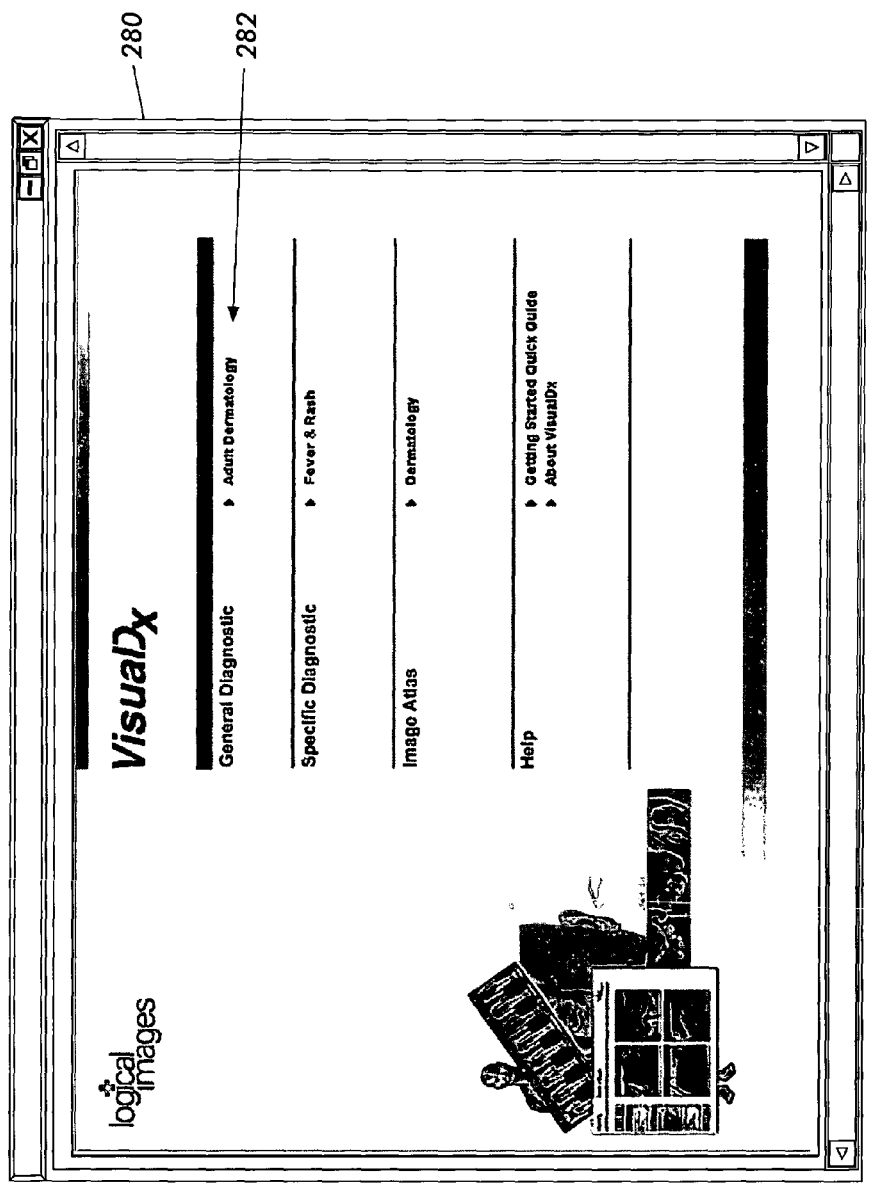
FIGS. 5-15 are illustrative examples of the user-interface for a visual diagnostic system implementing various features and aspects of the present invention in accordance with an adult dermatology embodiment.

Referring to FIG. 5, upon starting the VisualDx system software, a user may be presented with a user-interface screen 280 depicting one of a plurality of module selections, including but not limited to General Diagnostic and Specific Diagnostic modules. A user might access such modules through an upper-level menu or set of icons. Moreover, the menu selections may be displayed as a function of those modules for which the user and/or the user's practice, organization or company has subscribed. In the multiple-module environment, it is further contemplated that the modules and subscription offerings may be offered through the Internet or equivalent wide-area network from a common host location. Each of the modules would, to the extent possible, employ a similar user-interface "look and feel" in order to assure that a user familiar with one module will quickly become adept with using other modules. Moreover, the sum of the plurality of modules, when exhaustively developed, would ultimately result in a "complete" listing of possible diagnostic categories or constellation of findings. Also included on the initial VisualDx interface screen is the ability for the user to immediately proceed to review an image atlas (e.g., the Dermatology atlas) or to seek help in using the VisualDx software (e.g., Getting Started Quick Guide).

Figure 6:
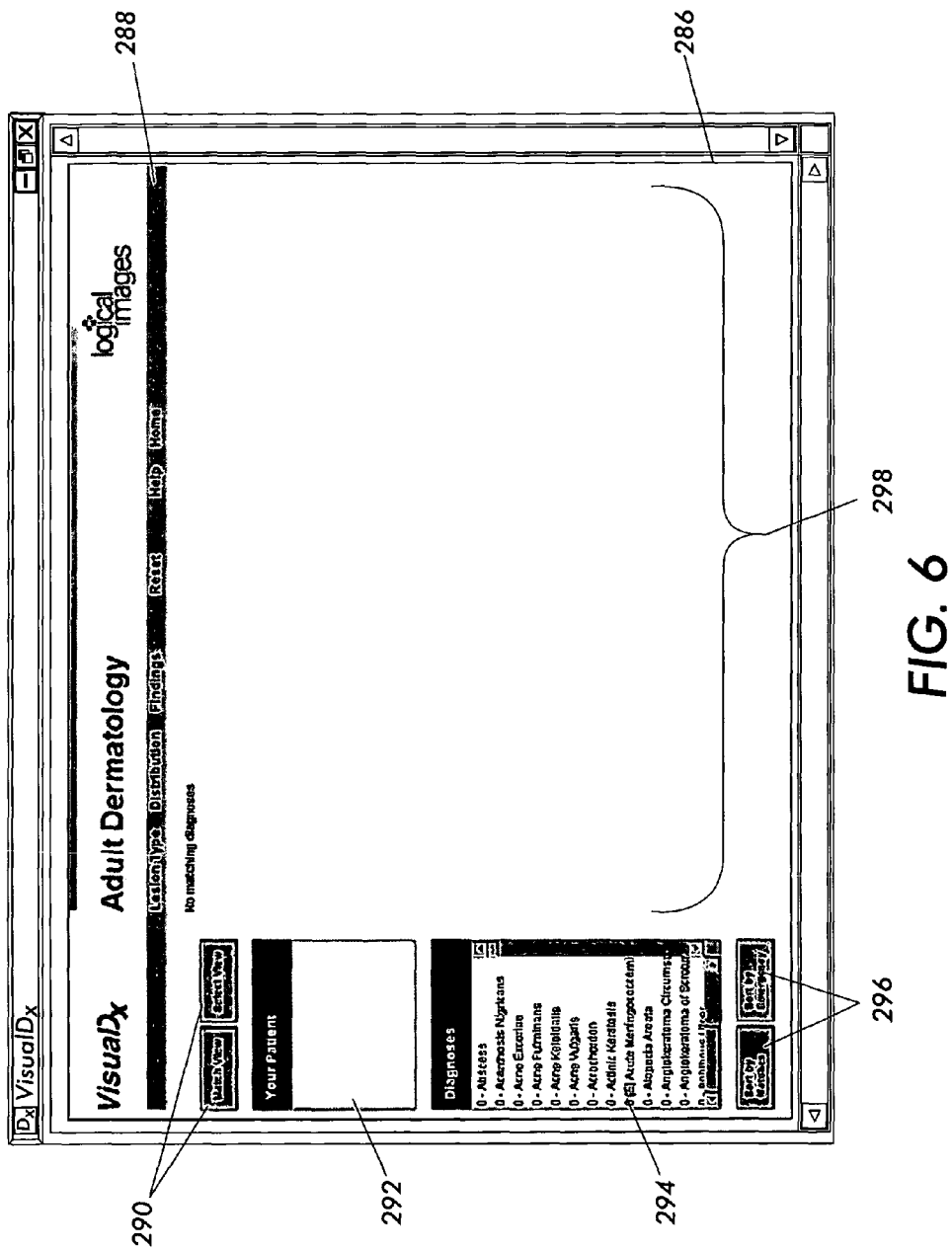

The VisualDx embodiment described herein will assume a user's selection of the Adult Dermatology Module, as a result of the user "clicking" on the "Adult Dermatology" link 282. The user's selection would, in turn, result in the presentation of screen 286 as depicted in FIG. 6. Such a screen, and the majority of the screens employed, depicts the look and feel of the VisualDx software. In particular, the user-interface screens employ a drop-down or pull-down menu bar 288 where, in the case of the Adult Dermatology module, the skin lesion type, distribution of the lesions, other findings, and additional menu selections can be made. Along the left side of screen 286, there are depicted view selection buttons 290, a patient findings window 292 and proposed diagnoses window 294. At the lower left of the screen, there are sort-type selection buttons 296. The functionality of the various buttons and windows will be described in further detail below. Of additional relevance is the fact that without any particular patient findings, no particular diagnoses are selected as a subset of matching diagnoses (all diagnoses are shown in scrollable window 294), and therefore no images or additional information are depicted in region 298 of the user-interface screen. However, the user may select from any of the diagnoses presented in scrollable window 294 in order to view the associated images. Such a feature provides functionality similar to an "index" or a "chapter" in a book, allowing a user to quickly view images related to one or more selected diagnoses.

Figure 7:
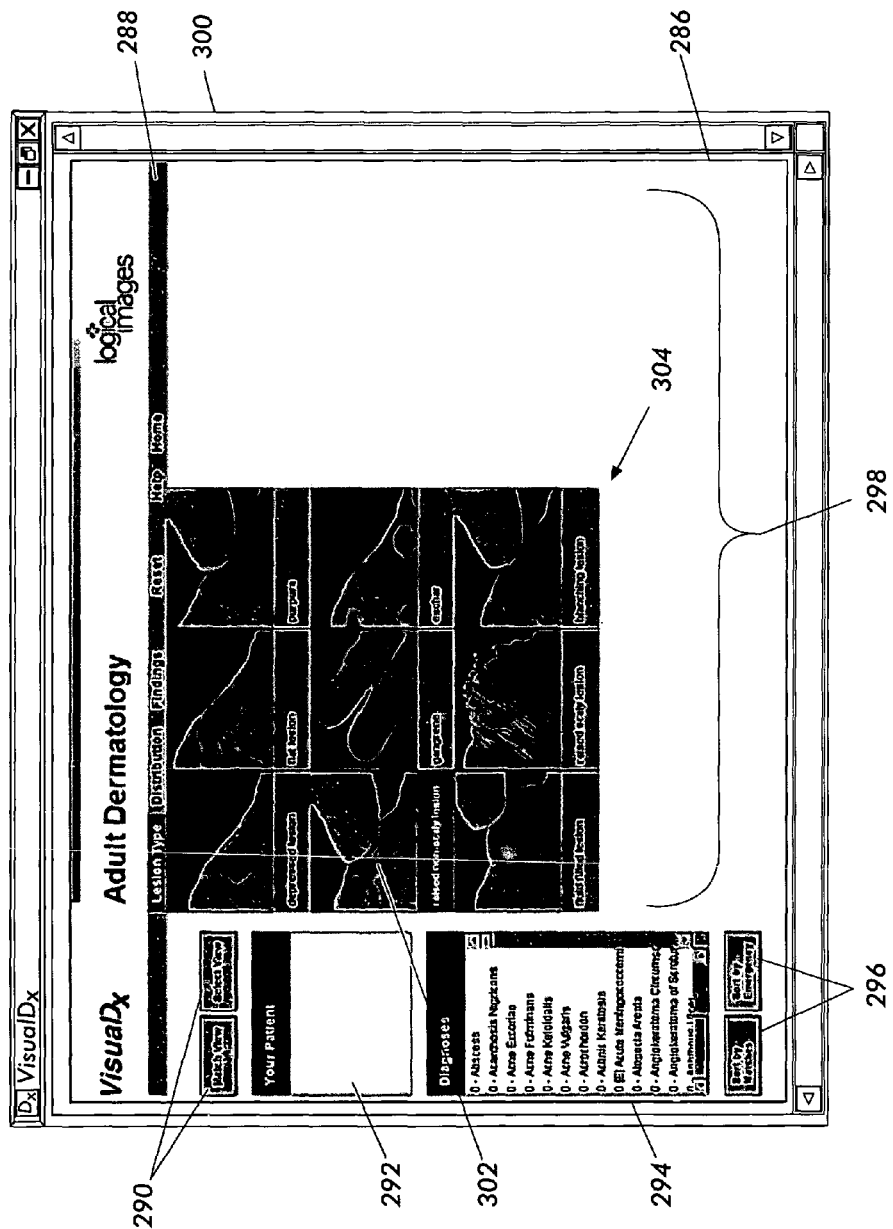

Referring next to FIG. 7, the preferred database has appropriate granularity and individual modules that are customized to use search fields relevant to the task of narrowing the visual diagnostic search. For example within the "Adult Dermatology" software module, it is sufficient to limit a visual search for vesicular (fluid filled) lesions using the term "fluid filled lesions."

Figure 13:
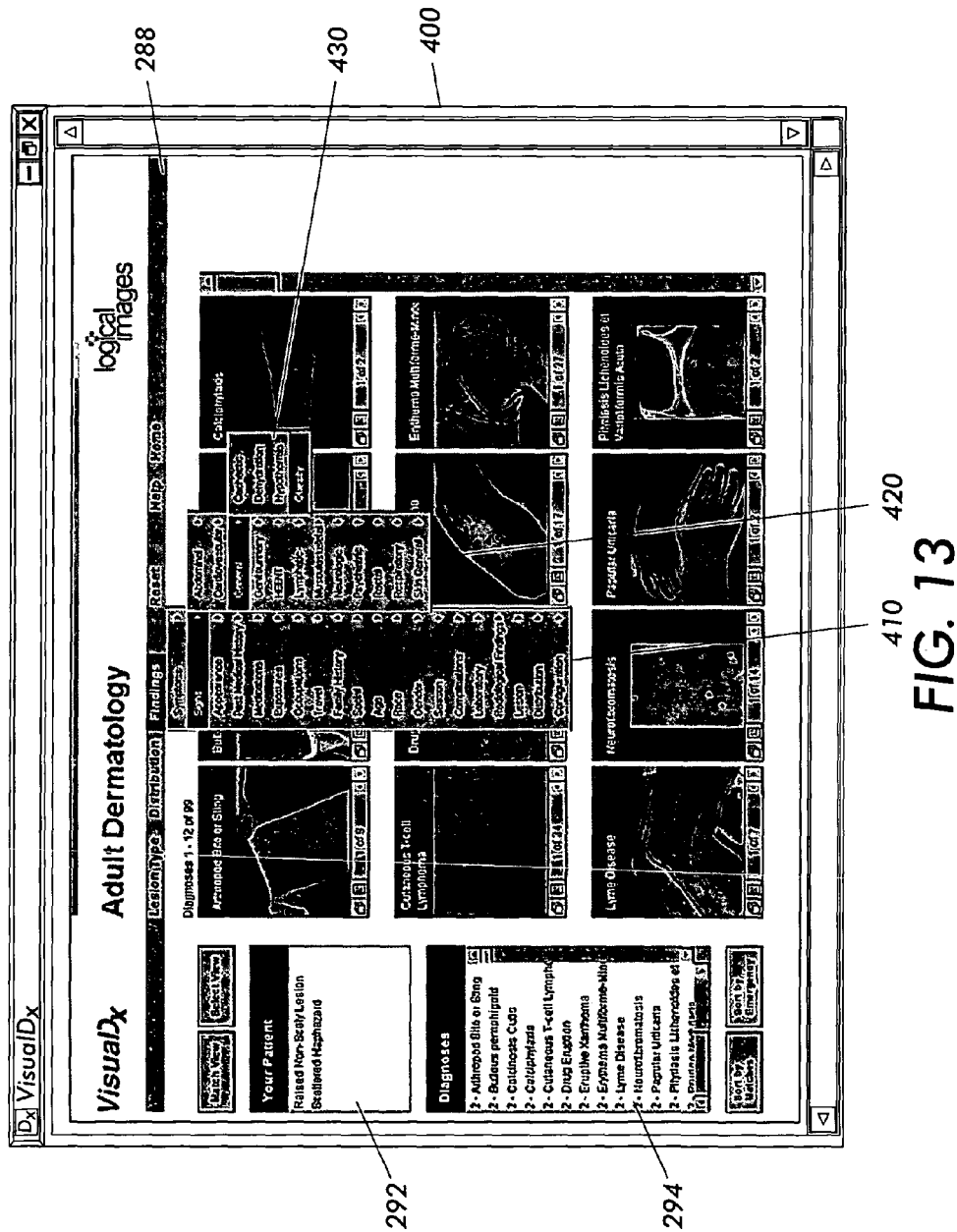

As a basic tenet of the design of the database structures of FIGS. 3 and 4, and the various user-interface screens described herein, the photographic or image icons (including diagrammatic, photographic, motion picture, thumbnail and iconic images) of particular diseases or diagnoses were required to be associated with findings. This was generally accomplished by an author knowledgeable in the field and was subsequently confirmed by an editor. Accordingly a preferred user-interface such as that depicted in FIG. 13 represents categories or constellations of findings in MS-Windows® enabled, pull-down menus or illustrates them on screens depicting detailed information about findings. In general, diagrams and artist's illustrations are believed to be more useful for higher, more abstract levels of a visual concept; for instance a finding subclass of "Skin Lesion" such as "Blister" or the distribution of the lesions on the patient's body. When dealing with more granular visual terms such as "Umbilicated Blister", photographic or image icons have more utility. These images are not be organized by case on the findings side as they are on the diagnostic side, though linkages back to the originating cases may be preserved as previously described with respect to the database tables in FIG. 3. Images and picons are preferably linked directly to the findings they represent.

Successful pattern-recognition dependent diagnosis in dermatology (and diagnosis within the other visually centered areas of medicine, radiology, pathology, ophthalmology, etc.) is determined by a host of factors, the most important of which is the examiner's ability to correctly recognize, define and sort visual findings into a well established classification scheme. Often specific visual clues correlate to a precise diagnosis; the ability to observe, classify and relate visual findings to pre-existing visual knowledge can result in split second diagnoses by the expert. Just as importantly, the present invention is believed to vastly improve the diagnostic capabilities of a non-expert primary care provider, whether a family practitioner, internist, pediatrician, OB-GYN, emergency medicine physician, nurse practitioner or physician's assistant.

For example, dermatologists speak of a primary morphology; this means the overall type of lesion without any secondary changes. These are elemental features such as a papule (a raised lesion usually less than 1 cm.), a vesicle (a raised, fluid filled lesion usually less than 1 cm.), a macule (a flat lesion usually less than 1 cm). These are examples of generic terms that are not very specific and at the most create a large diagnostic group. Lesions can be further classified by secondary morphology such as scale, crust, scab etc. that are generally the surface changes which occur on a primary lesion such as a papule. By saying a scaling papule one is slightly more specific, however, size, shape, color, location of the scale are further descriptors which lend precision and help to narrow the diagnostic consideration to a more manageable number. Further descriptive terminology used includes: number of lesions; shapes of groups of lesions; distribution on the body; color; etc.

As depicted in FIG. 7, screen 300 includes a pull-down, visual menu that is enabled by a user passing a pointer or cursor over the "Lesion Type" entry on pull-down menu bar 288. Doing so results in the display of the various icons and images in region 304 to illustrate the range of lesion types that may be selected by the user with a mouse or other pointing device. The pictorial representations allow non-expert users to select or input visual findings without prior knowledge of the specialized vocabulary associated with those findings, without inputting more granular terms, that would describe sub-types of fluid filled lesions, such as "umbilicated vesicles". On the other hand, a module designed for "Blistering Skin Disorders" will likely have detailed sub-menus for highly granular terms such as "umbilicated", "fluid color", "hemorrhagic fluid", "serous fluid", and so on. Hence, this level of granularity is not necessary in modules with very few diagnoses related to fluid filled lesions. A user's selection will be translated into queries on databases containing findings, diagnoses, images, and their relationships to each other as described herein.

It will be appreciated that the Adult Dermatology example described herein may not include each of the findings categories. Rather it employs a subset of the categories, wherein the subset comprises those categories deemed to be most significant in distinguishing and/or identifying possible diagnoses. The categories employed for VisualDx: Adult Dermatology are depicted in response to the user's selection of the "Findings" region on menu bar 288.

Figure 8:
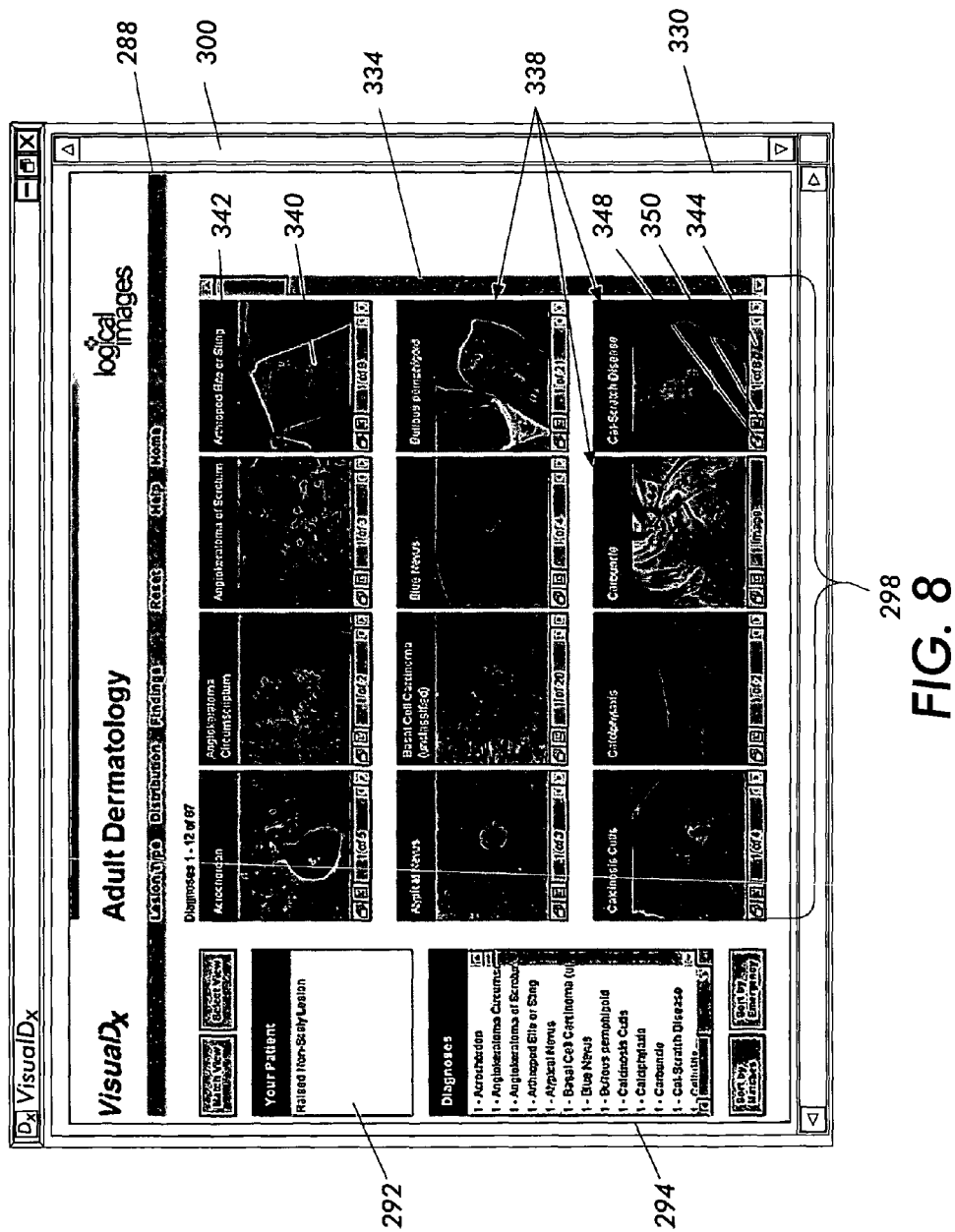

Considering the example of FIG. 7, upon a user's selection of a lesion type, say "rasied non-scaly lesion" in location 302 of lesion pull-down menu 304, the lesion type would be indicated as one characteristic of the patient. Subsequently, as a result of the user's selection of location 302, the user-interface screen of FIG. 8 would be depicted. Referring to FIG. 8, the lesion type selection is now reflected in user interface screen 330, where the patient findings window 292 has been updated to show the lesion type and where the possible diagnoses have been reordered to indicate those with a consistent lesion type (raised, non-scaly) in diagnoses window 294. Moreover, in region 298 of the screen, there is provided a scrollable image window 334. Within the scrollable window 334 there are depicted a plurality of diagnostic image windows 338, each of which includes its own functionality.

Figure 9:
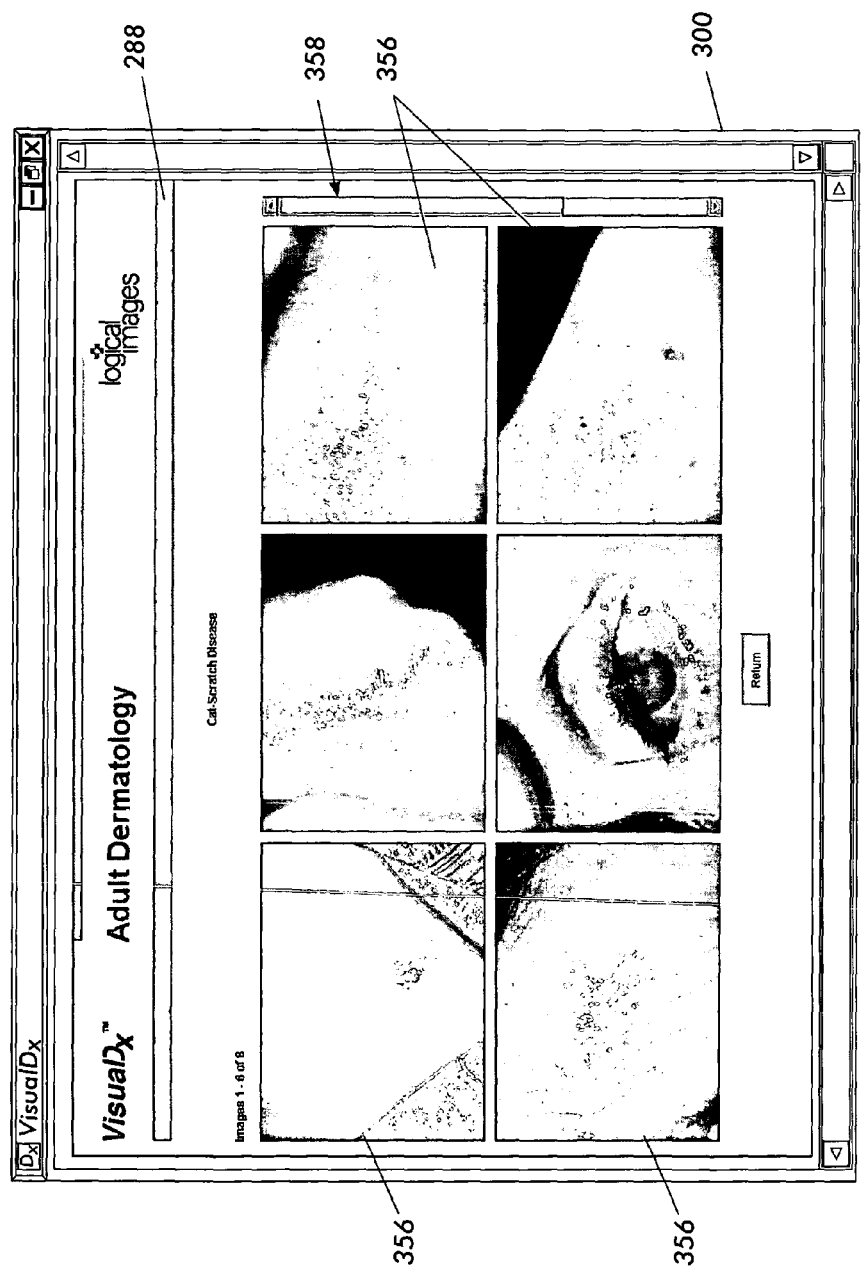
Figure 15:
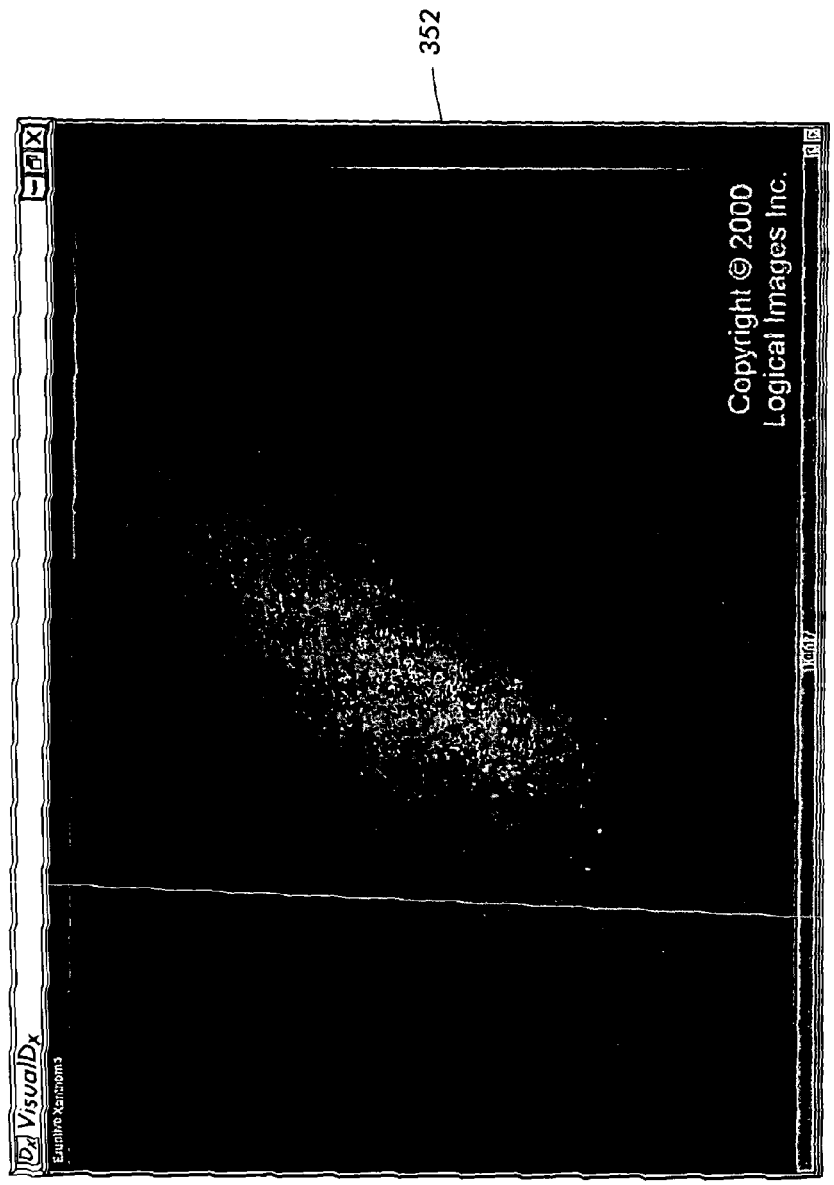

Windows 338 each include a central region 340 that displays a digital image depicting a diagnosed case of the disease indicated in title bar 342 associated with the window. Along the bottom of each window 338, there is an image control bar 344, where the central region of the bar indicates the number of images available for the particular diagnosis. Along the left side of bar 344 is an image stack button 348, allowing the user to view a plurality of images 356 in the image stack in scrollable window region 358 as shown in FIG. 9. As FIG. 9 illustrates, the images related to a particular diagnoses are displayed in a scrollable "contact sheet" where particular images may also be selected (clicking on the reduced size image) to display an enlarged, full-screen view as shown in FIG. 15. Returning to FIG. 7, detail button 350 changes the view of the user-interface to that depicted in FIG. 10, where region 298 includes not only a diagnostic image window 338, but also a scrollable text window 354 where a user may view further information and details related to a particular diagnosis.

Figure 11:
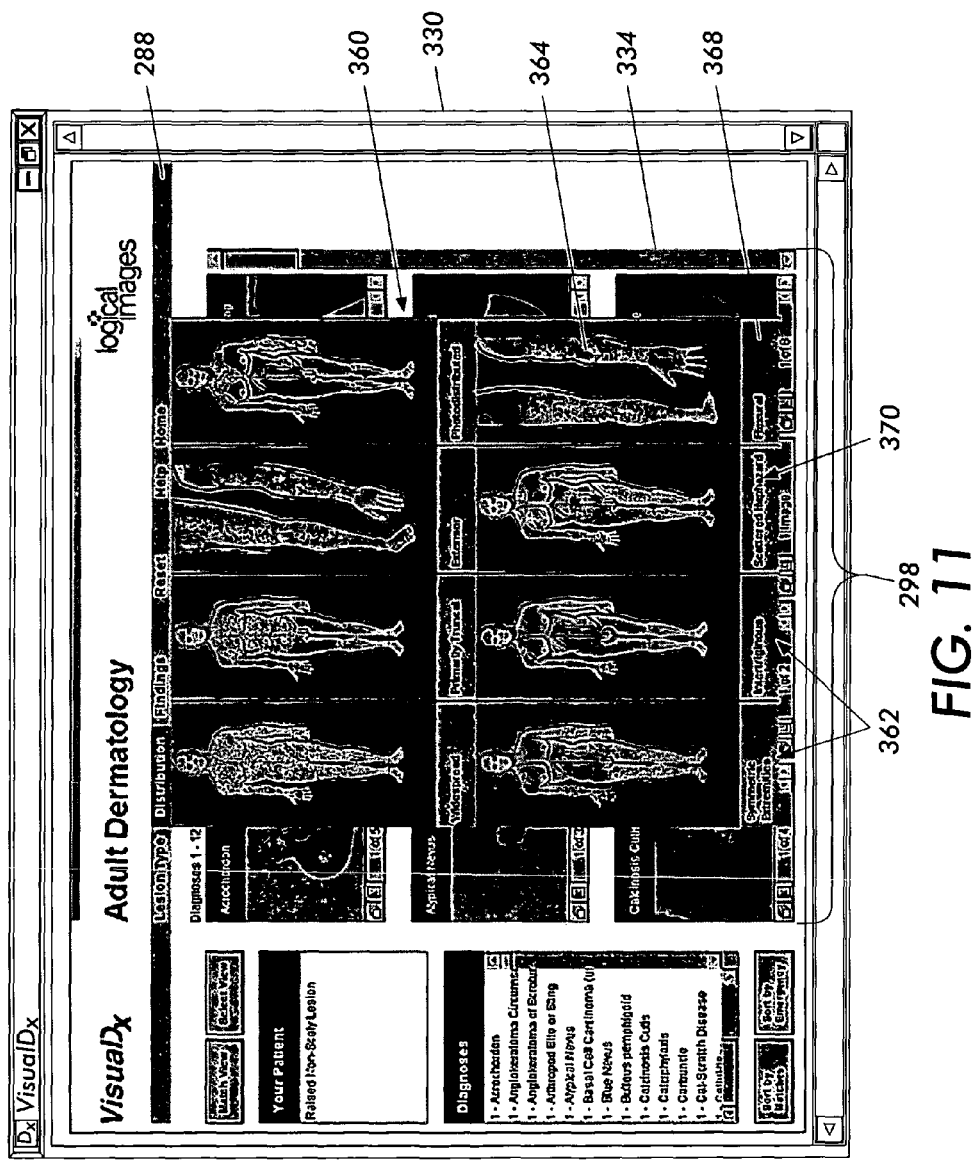

Turning next to FIG. 11, user interface screen 330 of FIG. 8 is depicted in a modified form in response to a user's selection of the "Distribution" item on menu bar 288. As a result of such a selection, pictorial menu 360 is displayed over the image window 334 in region 298. The pull-down pictorial menu 360 depicts various selections for the distribution of possible dermatologic rash patterns. In the menu, the individual selection regions 362 include a graphical representation of the distribution 364, along with a brief written description in region 368. Here again, the system, through the use of pictorial representations, allows a user to "match" a visual characteristic of the patient with a pictorial representation to add a characteristic (e.g., where the symptoms of the disease are distributed on the body). Assuming that a user were to select item 370 (scattered haphazard), the user-interface screen of FIG. 12 would be displayed.

Figure 12:
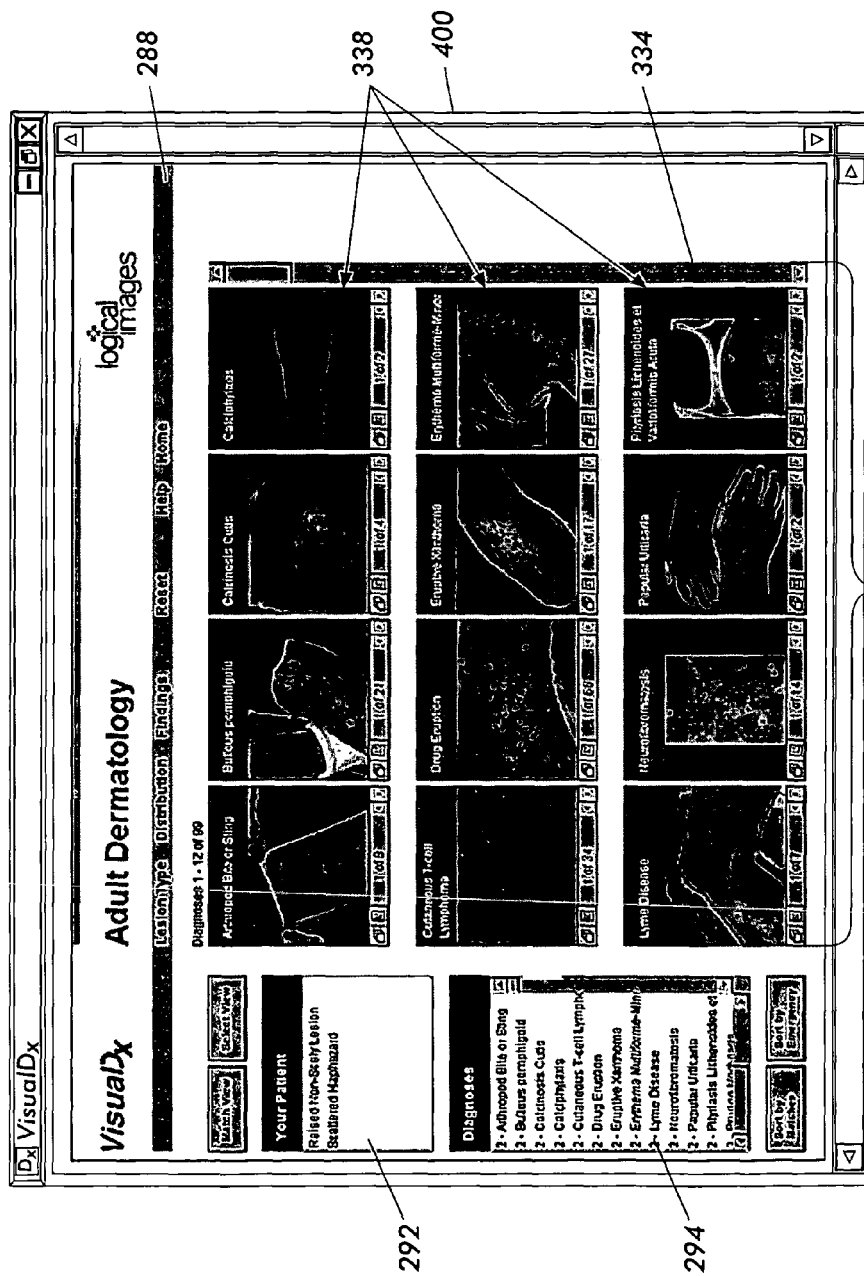

Turning to FIG. 12, user-interface screen 400 is depicted, where the distribution information selected by the user has been depicted in window 292. Furthermore, diagnoses window 294 now reflects, at the top thereof, those diagnoses that are consistent with the two patient characteristics currently input into the system—raised, non-scaly lesions, with a scattered, haphazard distribution. Similarly, the within scrollable window 334, there are depicted different diagnostic image windows 338. Again, the diagnostic image windows 338 are consistent with the possible diagnoses indicated in window 294.

In addition to the input of lesion type and distribution of the symptoms, a user may use the "Findings" selection in pull-down menu bar 288 to input one or more findings associated with the patient in order to further refine the possible diagnoses. Referring to FIG. 13, there is depicted an exemplary pull-down menu for the Adult Dermatology module. The different types of findings, some of which are illustrated by the pull-down menus 410, 420 and 430, have complex and rich hierarchies that are preferably expressed with separate database table structures for each type or category of finding. However, it is understood that equivalent database structures and methodologies may be employed in order to implement features and functions equivalent to those described and claimed in accordance with the instant invention. The types of findings employed in the various VisualDx modules or embodiments contemplated by the present invention include one or more of the following:

Signs
Symptoms
Travel History
Medical History
Surgical History
Family History
Age
Sex
Occupation
Exposures
Radiological Signs
Medications
Habits
Laboratory Findings
Cutaneous Signs
Morphology
Dysmorphology
Cutaneous Morphology
Distribution The rich, descriptive terminology of dermatology has a similar counterpart in the morphologic terminology of other visual specialties. For example, radiologists classify visual findings within categories such as density (hypodense, hyperdense etc), pattern (interstitial, etc.), location specific etc., and likewise pathologists utilize visual terminology corresponding to infiltrating cell types, colors, overall "architecture" of a tissue etc. found on the glass slide.

As another example, pathologists must correlate microscopic morphologic patterns into a diagnosis, which is often dependent upon a clinical history. It is typical for the pathologist to use the "clinical history" (which is found on the specimen submission slip) to help guide his/her interpretative process. Pathologists must look for shapes of cells, overall architecture of the examined tissue, color changes and interpret change within the context of the available patient findings. A hematologist, for instance, might receive a bone marrow biopsy to assist in the evaluation of a patient with an extremely low blood count. The patient history (findings) such as medical history of patient with prior history of malignancy, the medication(s) the patient is on, associated symptoms and signs such as jaundice are invaluable in helping the pathologist interpret the visual findings and provide diagnostic meaning.

Likewise, within the field of radiology, the radiologist is assisted when the referring physician provides a similar clinical history and associated findings. For example if the radiologist receives a requisition for a film or scan which says patient with HIV, productive cough, fever, he/she will consider in their diagnostic list a much broader range of possibilities for masses found on an abdominal computerized tomography (CT) scan, in comparison to a CT scan of a healthy seventy-five year old who has had a CT scan ordered to assist in the diagnostic evaluation of an acute episode of back pain. In this example, the findings of HIV, productive cough, and fever help shape and broaden the diagnoses under consideration and assist the context of the pattern recognition.

As noted above, a visually oriented specialist (dermatologists, radiologists, pathologists, ophthalmologists, endoscopists) spends several years honing his/her ability to correctly classify and relate the visual symbols to a knowledge base of diagnostic features, criteria etc. For a software system to present the same knowledge base in a usable fashion, where there are greater than one hundred possible visual clues, a hierarchical menu system is believed to be preferrable to facilitate searching of the picons. The image representations preferably progress from abstract or general graphical representations to computerized illustrations to photographic icons of more specific terms. In a sense the most critical step is to make sure that the user has found his/her way down the correct "branch" of the hierarchy (and to provide enough redundancy to assist the user if he/she has traversed an incorrect branch). Branching opportunities in such a system may be kept to a minimum number of screens, for example, lesion type, secondary morphology and configuration of lesion, and another screen to represent distribution of the lesion(s) on the body.

Returning to the exemplary embodiment depicted in FIG. 13, after selection of "Findings" in pull-down menu bar 288, a user is presented with an upper-level listing of findings categories as previous described. Movement of the mouse or pointer over one of the categories in menu 410 results in an adjacent menu 420 being displayed in a manner that is well-known in an MS-Windows environment. Ultimately, the menu depicted presents a series of selectable findings in menu 430. In the particular example depicted, the general "Signs" under findings is refined into a "General" category (menu 420) and ultimately a list of selections in menu 430 (cachetic, dehydration, hypothermia, and obesity). In the example, the user selection of "obesity" results in the user-interface of FIG. 14.

Figure 14:
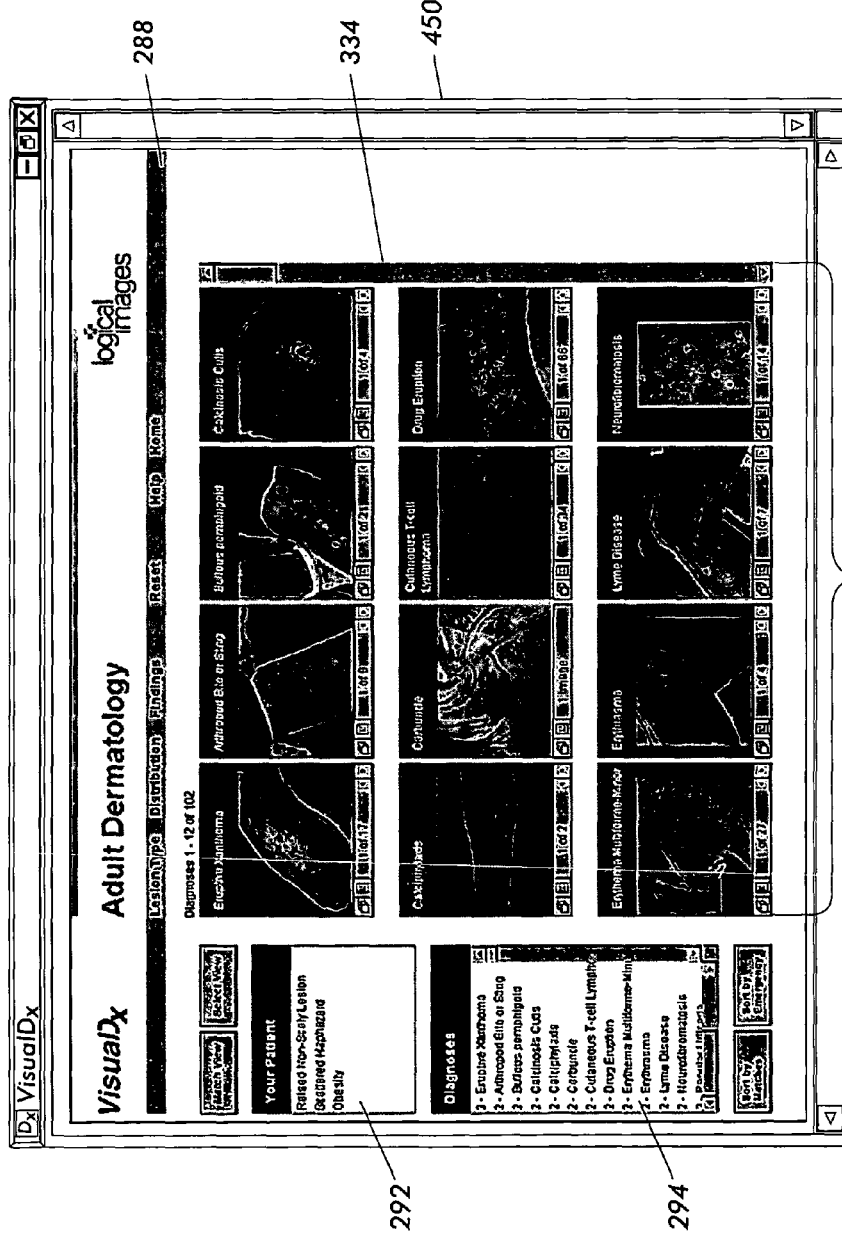

Referring briefly to FIG. 14, there a screen 450 is depicted where window 292 has been updated to add the "obesity" finding. Furthermore, the subset of diagnoses that are displayed, both in diagnoses window 294 and in the image window 334 (region 298) have been updated. In accordance with the invention described, the additional finding alters the subset of possible diagnoses and brings one or more possible diagnoses to the "top" of the list, where the subset is both displayed in window 294 in text form, and in window 334 in image form.

In a preferred embodiment, the browser-based visual medical diagnostic tool (VisualDX) implemented in accordance with an aspect of the invention is intended to allow both simple queries and complex, multiple-finding queries. The intention is to provide maximum flexibility for the user so that searching can be as simple as entering a finding such as a medication name, and viewing images of related drug rashes, or alternatively as complex as entering every possible patient finding (including symptom, sign, past medical history, exposure, medication list, laboratory findings, etc.). The user-interface, as described in accordance with the present embodiment, intends that each user will interact with the application in different ways, and even in different ways under different circumstances. The application software that drives the user-interface and interaction with the knowledge-base will not require that the user answer every question (look at every finding) in order to access the knowledge base. Rather, the software provides the possible diagnosis information (subset of the database) as the findings and characteristics are updated or altered by the user. The application therefore needs to display search results (diagnoses) dynamically. User input of each search term or patient finding, as depicted in the user-interface screen, preferably results in immediate re-listing and redisplay of the diagnostic list in window 294 and their related images in window 334.

As discussed, after inputting patient findings, the application program presents a list of possible diagnoses to the user. There will then be at least three basic options for viewing the images associated with the possible diagnoses:

(a) Users are able to view a results in the "contact sheet" format such as is depicted in FIGS. 8, 12 and 14, which include reduced-size image thumbnails in stacks, grouped by diagnosis. This interface represents one of the core functionalities of the present invention. As contrasted to a simple image database or image atlas, the diagnostic grouping of thumbnails allows the user to visually scan and review images in the context of diagnostic possibilities. Each diagnostic "stack" may also allow for a set of controls that permit the user to sort the images in the "stacks" by body location (this facilitates comparison of like lesions between diagnoses), "spread" out the stacked thumbnails so all thumbnails for a particular diagnosis can be viewed in a separate window (e.g., FIG. 9), and display the related findings for the diagnosis. Thumbnails will also be easily exploded into full screen images at a mouse click such as depicted on screen 352 in FIG. 15. It is also contemplated, in accordance with the image display, that the diagnostic image stack may be organized for display to depict a natural progression through stages of disease progression.

(b) Users may be able to select specific diagnoses from the diagnostic list window and then compare images from those diagnoses in a view contact sheet, also expanding images to full size as needed.

Figure 10:
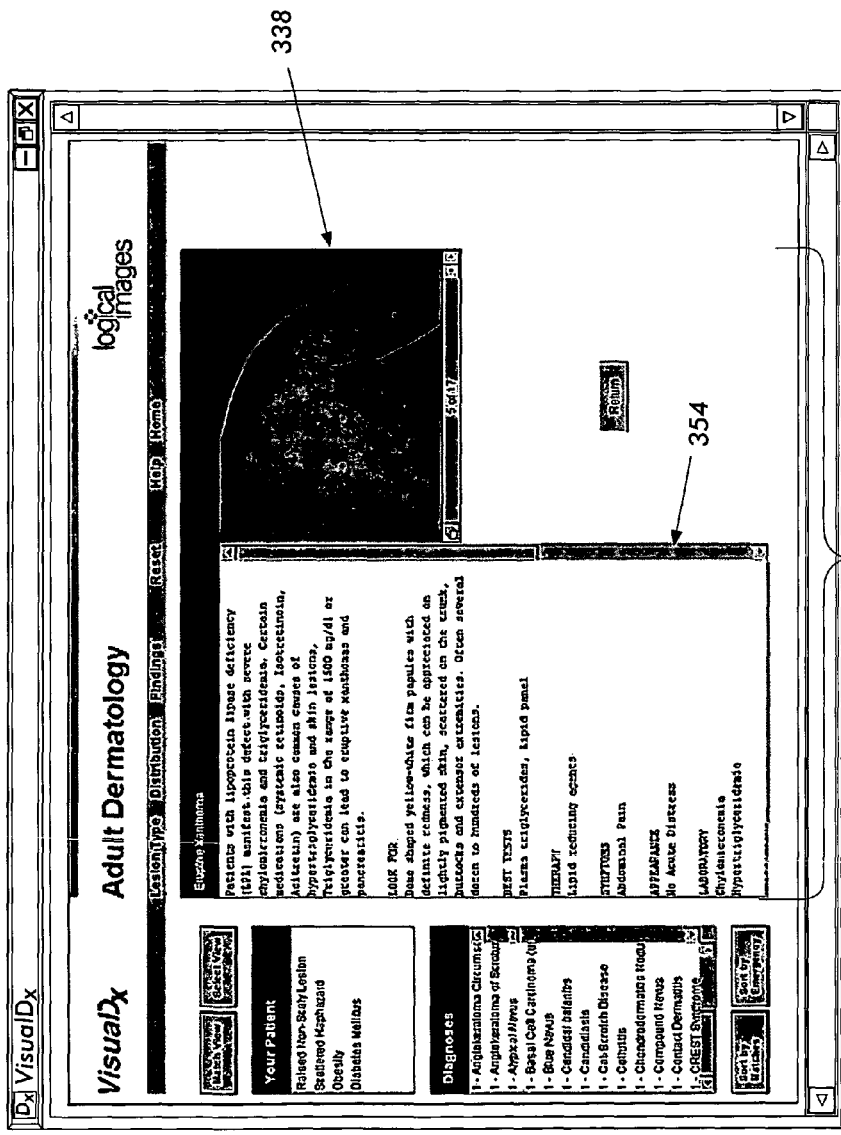

(c) Users may be able to select a single diagnosis and view images as well as information from a text window, both in thumbnail versions and full size (see FIG. 10).

Secondarily, the user may wish to access reference materials related to the diagnoses. Concise textual statements summarizing disease course, presenting symptoms and management options are available within the knowledge base, and are more particularly displayed as indicated in FIG. 10. Additional reference text may also be available through the Internet links such as Medline.

IV. Links Between Findings and Diagnoses

A tightly defined module will result in a concise knowledgebase with defined question pick-lists for the end-user. The association of a diagnosis with a module is based on a thorough review of the medical literature and is peer reviewed (author/editor) by experts in the medical field. A diagnosis can be in any number of modules. Construction of this knowledge base will have a cumulative effect: as modules are developed, diagnostic profiles will be leveraged into new modules.

In order to identify diagnoses from a set of findings, the present invention preferably expresses the linkage from finding to diagnosis with finding-diagnosis-links (see Diagnosis_Finding link table 258 in FIG. 4). The Diagnosis_Finding link s are organized by the type of finding they fall into. The example described herein finds the set of Diagnosis_Finding link's in the finding_type table linked to a working set of symptoms, signs, travel history findings, etc., and then produces the set of diagnoses. The relationships to findings are two-way and many-to-many. In other words, a diagnosis can have many associated findings, of all different types of finding, and a particular finding can be found across many diagnoses.

In a preferred embodiment, the Diagnosis_Finding links express the existence of a relationship between findings and diagnoses. These relationships can be used to organize the visual presentation of information, or direct the search for related information. The relationships contemplated by the present invention include "is associated with", "predisposes", "exacerbates", "complicates", "is a complication of", "causes", and "is caused by." They are important in the areas of occupation and exposures, family and medical histories, and medication use. They are primarily applicable in elucidating diagnosis-to-diagnosis relationships, so they are of the most use where a finding for one diagnosis implicates another one.

For example, an "Exposures"-to-diagnosis link relationship is exemplified by tobacco smoking as a risk factor for lung cancer. In the finding_type for "Habits", a finding of "Smoking" would be in the relationship of "Predisposes" to a diagnosis of lung cancer. A diagnosis-to-diagnosis link is exemplified by the relationship between lung cancer and pneumonia. A complication of lung cancer could be pneumonia. From the other side of the relationship, lung cancer predisposes the patient to pneumonia. In the finding_type for "Medical History" a finding of pneumonia would point to lung cancer as a predisposing factor. Also under "Medical History" a finding of lung cancer would point to a possible complication of pneumonia. It is believed that a system structured in this manner will represent the temporal relationships in medicine and will provide a rich connectivity among findings and diagnoses and their associated database objects.

In a preferred embodiment no probabilities evoking strengths or frequencies, based upon statistical or probabilistic approaches, are included in the knowledge base to help users arrive at a likely diagnosis. The Diagnosis_Finding link table contains a "diagnostic importance" field to contain information about relative importance of a finding in a diagnosis, as an aid to the user. In one embodiment, each Finding_Diagnostic record is classified, at the time of data entry, in the following three categories:

Major or common finding for the diagnosis;
Minor or infrequent finding; and
Case report finding or very rarely seen.

Additionally, findings are flagged to signify whether they are officially accepted criteria for making a diagnosis. An example of officially accepted criteria would be the American Rheumatologic Society criteria for diagnosing Lupus erythematosus, a de facto standard. Since the application programs are not expected to attempt diagnosing on their own, this very imprecise "importance" data is not being used in application programs to automate weighting of query results. The diagnostic importance is intended to be derived by the practitioner, from being able to re-sort the diagnostic list by applying accepted diagnostic criteria, major findings only or total finding views which include the minor findings and case report findings as well. In general, however, this data may be furnished to inform the end-users and help them form impressions about how seriously they need to consider the presence or absence of a finding when looking at a potential diagnosis.

V. Diagnoses/Identifications

In the VisualDx system, diagnostic modules accept input from users and produce a list of diagnoses that match or partially match the input. Searches for diagnoses may occur through two basic approaches: querying for diagnoses matching textual findings; and querying for diagnoses matching visual findings.

Input of textual findings may be via free text entry, or preferably from a hierarchical pick list in the form of a dropdown menu presented to the user. Free text entry may present the user with all partially matching findings when an exact or synonymous match does not exist. As implemented, and described above relative to dropdown menus in FIG. 13, findings lists may be organized into a hierarchy of categories to minimize the number of choices presented to the user at one time during the selection process. In one embodiment, the findings categories are determined by reading the hierarchical relationships from a database and may, accordingly, be dynamically generated upon updating of the database. It will be appreciated that certain findings may also include or specify relative comparisons of numeric data (e.g. "creatinine elevated" level) shall specify a precise value to the user (e.g. "creatinine elevated, >1.8").

Accordingly, it is contemplated that a textual findings interface screen, in addition to the dropdown pick-lists 410, 420 and 430 and summary window 292 in user-interface screen 400 if FIG. 13, may contain a free text entry area and other navigational tools. As the nature of the findings may include visual and textual information, any combination of textual and visual findings may be allowed in a search. As a result of any selection, a search may be initiated and a display of matching and partially matching diagnoses will be displayed as depicted, for example, in FIG. 14. This display may be updated any time a finding is added, modified or removed.

In one embodiment, the images associated with a particular diagnosis are related as a "stack." The images in a stack may be sorted based on closeness of view, body location and lesion type. The user may be able to select which sort method is used, although a default may be used for actively displayed image stacks, where the default may or may not be related to a lesion type or other defined finding.

Displaying images of suggested relevant diagnoses (or identifications in the non-medical embodiments) is a central objective and focus of the present invention, including its knowledgebase and applications thereof. Diagnoses may be displayed textually and/or visually. The text will be contained in the diagnosis records. As described, the visual display of diagnostic information is through links to images associated with the knowledge base. In the embodiments described, diagnoses have a summarizing picture icon, usually a close-up view of the most visually defining characteristic, abstract icons or designated characteristic thumbnail images for situations where many diagnoses are arrayed in a menu.

Diagnoses may be sorted for display in accordance with a user-designated preference (e.g., matching or emergency order). They will sometimes need to be sorted into broad categories. Under those broad categories or when coming up in search results associated with a set of input findings, they will need to be sortable on their various attributes. The user may also change the sort order in real-time to assist in the process of surveying the results and refining the search. Diagnoses, at a minimum, should be sortable on one or more of the following:

Numbers of matching findings (the default sort order)
Severity of disease (emergency or non-emergency)
Pathophysiology (infectious disease, malignancy, genetic disease etc.)

Types of matching findings
Classes of disease, and
Numbers or classes of non-matching findings A default sort order for displaying diagnoses, Numbers of Matching Findings is believed to be the best way to show how well a diagnosis fits the current set of findings. Each time an additional finding is designated by the user, the knowledge-base query is rerun in order to update the display, so the user knows immediately how closely every diagnosis in the module matches the chosen set of findings.

Because non-matching findings may contain information vital to the diagnostic process, the preferred embodiment allows the natural process of displaying the set of findings related to the diagnosis. For example, FIG. 14 depicts findings (in patient window 292) that correspond to the particular diagnoses indicated. This allows the user to determine which of the findings for a given diagnosis had not been selected or indicated in the initial search.

The immensity of the field of medical knowledge and the specialization of practitioners dictates the creation of focused applications for the knowledge base structure described herein. Diagnoses are classified as belonging to problem oriented modules so that focused subsets of the knowledge base can be quickly viewed by the user. Additional modules that are possible, include:

Simple eye and eyelid guide for the generalist;
Simple ear nose and throat guide for the generalist
Pediatrics;
   Neonatal skin disorders and premature baby visual guide
   Skin disorders of infancy
   Congenital abnormalities noted at birth (structural)
   Generalized rashes and exanthems of infancy and childhood
   Localized skin problems and tumors in children
   Disorders of the scalp and hair (infant through childhood)
   Hemangiomas and vascular disorders in children
   Nail problems
   Localized skin problems including genital lesions
Geriatrics
   Elderly skin problems
   Skin ulcers and skin care
Genetics
   Congenital syndromes childhood and adult
   Craniofacial Anomalies
Occupational medicine
   Contact dermatitis (Occupationally related skin allergy)
   Performing arts/Sports medicine
HIV
   Skin problems in HIV and AIDS
Birthmarks
   Hemangiomas (Before and after)
   Melanocytic Nevi (Before and after surgery for patient info)
Wound care
   Burns
   Injuries
   Amputee care
   Trauma
Infectious disease
   Travel medicine (a guide by country to skin and infectious disease prevalent in each country)
   Male Genital Lesions including sexually transmitted disease
   Female Genital Lesions including sexually transmitted disease
Diabetes
   Care of diabetic ulcers and skin
Adult Dermatology for the generalist
   Hypopigmented and Hyperpigmented diseases (flat lesions)
   Papular and Plaques (raised lesions)
   Ulcers and atrophy (depressed lesions)
   Vesicular and bullous diseases (blistering lesions)
   Purpura and hemorrhagic lesions
   Individual Lesions or Tumors
   Skin manifestations of internal disease
   Genodermatoses (Heritable skin disorders)
   Nail Diseases-Adults
   Ethnic Skin disease
   Acne and related disorders
   Ostomy care
   Hair and Scalp Problems
Environmental Exposures
   Infestations and Bites (with images of organisms, spiders etc)
   Marine and Aquatic Injuries (and images of organisms)
   Botanical dermatology (and images of plants causing disease)
Body Region Specific
   Disorders of the palms and soles/Disorders of the feet
   Oral mucosal lesions including the tongue
   Intertriginous region (axillae, inguinal, inframammary)
   Tumors of head and neck
   Facial Rash
Patients with specific risks
   Transplant and immunocompromised patients
Forensic Medicine
   Autopsy/Cause of Death
   Crime Scene Analysis VI. Alternative Embodiments Having described the details of the present invention in terms of a visual, medical diagnostic system (VisualDx), particularly an Adult Dermatology embodiment, the following description is directed to additional, alternative embodiments in which the present invention, or aspects thereof, may find particular application.

Figure 16:
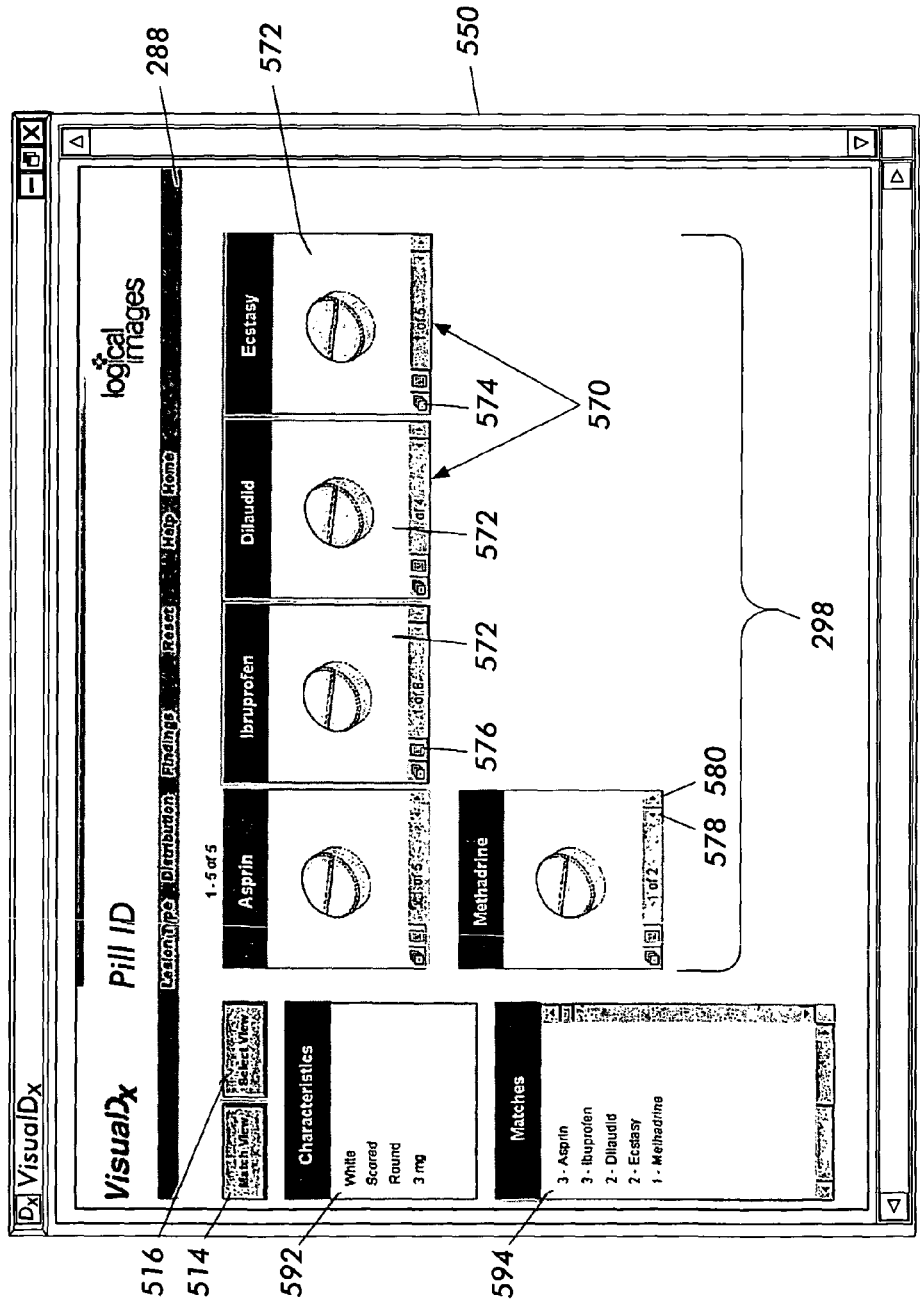
FIG. 16 is an illustrative example of a user interface for a pill identification system for the purpose of explaining an alternative embodiment of the present invention.

Turning to FIG. 16, there is depicted a particular alternative embodiment contemplated for the present invention, and application referred to as Pill ID.

Again, it will be appreciated that one or more aspects of the Pill ID, or other embodiments described herein, may be implemented in a similar hierarchical menu/list methodology. For example, it may be possible to implement the following hierarchy for presentation to a user to assist in the identification of street or other dangerous drugs:

Upper Level Menu List:
   form, method of administration, markings, color, shape, gross weight,
   location of use, user symptoms, primary chemical composition
Second Level Menu List
   form->
      powder, capsule, tablet, liquid, patch, gaseous;
   method of administration->
      oral, injection, epidermal, smoking/inhalation;

Referring to FIG. 16, the various elements of the user-interface screen 550 being consistent in functionality to the description above, there are also depicted a series of images 570, where each image depicts a possible matching pill based upon the characteristics entered or selected by the user. Each window in region 298 further includes not only an image 572 but also a stack spread button 574 and a text display button 576. Selection of the stack display button 574, under any particular image, will result in the images in the "stack" being displayed in the interface as previously described with respect to FIG. 9 of the VisualDx embodiment. Selection of the text display button 576 will produce a text window with descriptive details and other information related to the particular pill. Also depicted under each image are stack navigation buttons 578 and 580 that may be used to move backward and forward, respectively, through the stack of images for a particular pill. For example, a stack of images may include not only various brands of the pill, but also may include alternative views (back, side, etc.) so as to improve the likelihood that a user will be able to identify a particular pill.

It should also be appreciated that, in one embodiment, it will be possible to "double-click" on an image, no matter the view in which it is presented, to present the user with a full-screen, high-resolution view of that particular image. Subsequent clicking or selection of the full-screen image will then return the user to the previous view or screen. Alternatively, navigation arrows allow the user to sequentially view higher resolution images in a full-screen display mode.

Continuing to refer to FIG. 16, the system depicted by the user-interface screen 550 may be employed for cross-referenced access to image and knowledge databases for the purpose of assisting in the identification of street and other drugs. It will be appreciated by those familiar with digital imaging technologies that such a system may require a standardized or controlled system for imaging and reviewing visual information. In particular, the system may include an imaging station, where a sample or specimen of the drug is placed into a cabinet or container having a specimen platen or platform, illumination and a high-resolution, color digital image capture device (digital camera, CCD scanner, etc.). Such a system may take the form of the characterization peripheral 74 indicated in FIG. 1.

One aspect of the present invention contemplates a system for cross-referenced access to image and knowledge databases for the purpose of assisting in the identification of street drugs. The system, as described above, would include a user-interface to solicit a plurality of characteristics of a sample from a user. For example the characteristics might include the form of the drug (powder, capsule, tablet, liquid, patch, gaseous), method of administration (if known) (oral, injection, epidermal, smoking/inhalation), markings, color, shape, gross weight in (mg), size in (mm), geographic location of use, user symptoms, primary chemical composition (determined through commonly used drug tests employed by police officers, such as the Marquis Test, Mandelins Test and the Liebermans Test). Based upon the characteristics indicated by a user, a diagnostic engine similar to that employed for the VisualDx system, would then identify, from a plurality of possible street drugs, a subset of street or other dangerous drugs that are consistent with the characteristics. Using the subset of street drugs, an information space of the image database could then be sorted for presentation to the user, wherein the presentation is accomplished through the concurrent presentation of images for user review in the identification of the street drug.

In the case of street drugs such as pills, it is further contemplated that such images would be of a standard size, photographed against a defined background (in the case of pills), perhaps including a 2.5×2.5 cm grid imprinted thereon to aid a viewer in assessing the size of the pill. This standard reference image would then have the pill represented uniformly in the lower right hand corner so that the user could have an immediate standard visual reference for comparison. Textual information regarding product or chemical name or ingredients, symptoms, treatments (if any), additional tests to identify substance would also appear in response to the user's selections on the interface screen.

In addition, a second aspect of this embodiment would be to prospectively collect information from users of the Pill ID system to augment the database (street drug appearances are changing all the time). This set of users (forensic chemists or other crime lab personnel, drug enforcement investigators, other public safety or police personnel) would have an imaging terminal/station or alternatively a standard set of photographic guidelines and techniques to perform for image acquisition (standard grid, lighting, backdrop, item position on grid, and distance from object). Subsequently, images acquired using the system or method would then be sent electronically to a centralized image database, along with additional characteristic details (weight (mg), size (mm), laboratory analysis results, date item received (e.g., date/time stamp), number of items seized, location (jurisdiction), product name, listed contents (from label if in a container). The centralized database would also be a searchable database in the same manner as the previously described invention (with the addition of searching and display of geography, to follow the spread of specific drugs from locale to locale, for instance).

Furthermore, in addition to providing image data from a database, such a system may also include means for a side-by-side comparison of the actual sample image information with that of database image information. As described above, specimen or sample data may be added to the database in order to continue to increase the information retained therein. For example, a street drug previously unknown in one region of the country (e.g., Cincinnati, Ohio or Rochester, N.Y.) may be identified by its visual characteristics as being similar to drugs manufactured in another region (e.g., Toronto, Canada). Alternatively, an unknown street drug may be added to the database once its analysis, including chemical composition, is complete.

The preferred system utilizes a user-interface with which a user may enter a descriptive characteristic of a sample via a series of pull-down menus such as those illustrated in menu bar 288 of FIG. 16. Such characteristics may also include: form (powder, capsule, tablet, liquid, patch, gaseous), method of administration (oral, injection, epidermal, smoking/inhalation), color, geographic location of use, user symptoms, and chemical composition. Once entered, a diagnostic engine within the system would process the information entered to identify, from a plurality of possible street drugs, a subset of street drugs that are consistent with the characteristics input by a user. Then, using the subset, reorganizing an information space of the image database for presentation to the user via the user interface, where the presentation is accomplished through the concurrent presentation of images for user review in the identification process.

It is further anticipated that the information collected by the system would be shared with the crime labs and law enforcement agencies where the information about the positive identification of the pill's chemical nature is then appended, so as to be of value to emergency department personnel, first responders (or other interested people, such as camp personnel, schools, etc.). It is believed that such a system would assist in tracking the geographic spread of new illegal drugs, perhaps helping with identifying sources (in LA, versus NY, versus Canada) and shutting them down.

As an example, the prospective capture of the picture of a pill and its logo or mark (linked to a database that includes other information such as the quantity, location, identity of person, circumstances of capture) can be performed at the police precinct. The identity (chemical nature of the pill) is then confirmed at the crime lab. The database continually grows and is available through multiple jurisdictions. Warnings about the release and spread of new dangerous drugs would be timelier; as such information could be shared across a secure network connection with other state, national, or international law enforcement agencies.

In yet a further alternative embodiment, the one or more aspects of the present invention are believed applicable for use by a coroner or medical examiner in the investigation of a death. Here again, the system may be used in conjunction with traditional equipment and techniques, providing a coroner or medical examiner with a resource to aid in the investigation. More specifically, images may be employed when investigating gross and microscopic pathology at autopsy; gross external images including signs of trauma, natural causes, inflicted injuries; gross internal images of diseased organs and injury; and microscopic images of diseased tissues. In implementing such a system, characteristic search fields might include: Trauma type—blunt, laceration, gunshot, etc.; Laboratory information—drug screen, chemistries, blood count; and other information such as dental records.

In particular, a system for cross-referenced access to image and knowledge databases for the purpose of assisting in the investigation of a death might include a user-interface to solicit a plurality of characteristics of the death. Additional characteristics would likely include: manner of death (accidental, natural, suspicious), weapon type (for guns, for instance handgun, shotgun rifle, homemade, assault weapon, machine gun), sub-wound (gunshot close contact burns, etc.), iconic representations of wound (hole size, slash pattern) modality (appliance or object involved in death e.g., gun, train, fire), medical lexicon (acute, chronic, obese). Based upon the characteristics, a diagnostic engine is then employed to identify, from a plurality of possible causes of death, a subset of causes that are consistent with the characteristics. Then, using the subset of causes, an image database may be organized for presentation to the user, wherein the presentation is accomplished through the concurrent presentation of a plurality of images for user review in the identification of the cause of death.

As in the prior embodiments, once a user enters the data, a pre-programmed diagnostic engine would be employed to process the characteristics entered to identify, from a plurality of possible causes of death, a subset of causes that are consistent with the characteristics and description entered. Using the subset of causes, the information space of the image database would be reorganized for presentation to the user, wherein the presentation is accomplished through the concurrent presentation of images for user review in making a determination of the cause of death.

Yet another alternative embodiment contemplated for the present invention is for cross-referenced access to image and knowledge databases for the purpose of assisting in the identification of plants, fungi or other living organisms (e.g., reptiles, arthropods, etc.). With respect to plants and fungi, the system would include a user-interface to solicit a plurality of descriptive characteristics of a plant sample (including fungi such as mushrooms) from a user, including size, shape (leaf, seed/berry, flower, fruiting body, etc.), vein pattern, coloration (leaf, stem, root, color in Fall), stem type (woody, vine), where found, etc. Once such information had been collected in a manner consistent with a standardized nomenclature, the diagnostic engine would be used to identify, from a plurality of possible plants, a subset of plants that are consistent with the characteristics entered. The subset of plants would then be selected from the database and presented in an information space wherein the presentation is accomplished through the concurrent presentation of a plurality of images for user review in the identification of the plant.

Further embodiments in which aspects of the invention may find use include the diagnosis and treatment of Plant and Garden Problems. For example, people often do not understand the cause of change in the appearance of what was a healthy plant, lawn, ornamental shrub or tree. A combination of textual and visual clues could be similarly used to help the person identify the cause of the change and solve problem.

As described above, the system has particular application to human dermatology. However, there may also be particular application to Veterinary Dermatology, where the present invention may be employed in the diagnosis of animal skin and infectious disease, cutaneous signs of systemic disease, etc. Accident Investigation (Aviation, Automobile, Military) may also be assisted using the present invention, where patterns or characteristics of auto accidents, (e.g., the recent tire safety issue as an example) may be employed to arrive at a determination of the cause of the accident. Factors such as skid marks, damage to vehicle, injury to passenger and other factors could be used to assemble cases with stacks of images.

Alternatively within the aviation industry, the precise cause of accident may not immediately be known, and cataloguing evidence of metal fatigue, and damaged parts in association with the metadata and particulars of accident would allow for more efficient review of the "visual clues". Similar to medical diagnosis, ambiguity and uncertainty is the rule, therefore "cases" could be similarly assembled and viewed to help the user identify accident causes and arrive at a final determination. In a similar fashion, police crime scene investigation may be facilitated by aspects of the present invention. In Police Detective work, an investigating officer may be tasked with assembling all clues of a crime, associate visuals (footprints, fingerprints, signs of breaking and entering, pictures of suspects) with textual data of crime: location, time, victims etc. The details of the crime may then be accurately cataloged and accessed using the present invention.

In recapitulation, the present invention is a method and apparatus for increasing the usefulness of visual knowledge in a number of applications. It distills the relationships between characteristics and hypotheses into database form, thereby organizing visual information in a manner suitable to aid the user in the investigation of the various hypotheses (pill identification, plant/animal identification, cause of death, cause of accident, etc.). The invention has enormous potential because it sidesteps unresolved issues around knowledge engineering by not automating a decision making process. Rather, the present invention is an aid to assist a user test and reach a reasoned conclusion based upon information available by direct observation and comparison with stored image and textual data.

It is, therefore, apparent that there has been provided, in accordance with the present invention, a method and apparatus for a cross-referenced knowledge and image database wherein a plurality of hypotheses are employed to narrow and create at least one subset of possible identifications that are displayed in at least an image-centric format for further consideration by a user. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A system to aid a user in a visual diagnostic process, comprising:

a computer system;

an image database, accessible by said computer system;

a knowledge database, accessible by said computer system, cross-referenced to said image database, for the purpose of assisting in the diagnostic process, said knowledge database including a plurality of findings-diagnosis links representing relationships between findings and diagnoses;

a user-interface attached to said computer system to solicit, from the user, a plurality of descriptive characteristics of a sample requiring diagnosis;

a diagnostic engine operating in said computer system, responsive to said descriptive characteristics, wherein said characteristics of the sample are employed by said engine to automatically identify, using the findings-diagnosis links, a subset including a plurality of possible diagnoses that are consistent with the characteristics; and using the subset of diagnoses, automatically reorganizing an information space of said image database for concurrent presentation on said user-interface of a plurality of images representing the subset of possible diagnoses for user review via the user-interface.

2. The system of claim 1, wherein said diagnostic engine operates dynamically, using the subset of possible diagnoses, to reorganize the information space in response to modification of at least one of the plurality of descriptive characteristics by the user.

3. A method for aiding a visual diagnostic process, including:

creating an image database from a collection of images pertaining to a particular subject matter, said image database residing on a mass storage device operatively associated with a computer;

creating a knowledge database with other data related to the particular subject matter, wherein said knowledge database includes a plurality of findings-diagnosis links representing relationships between findings and diagnoses and is cross-referenced to said image database, for the purpose of assisting in the diagnostic process;

collecting from a user, through a user-interface adapted to the particular subject matter, a plurality of descriptive characteristics of a sample requiring diagnoses;

a diagnostic engine, in response to said descriptive characteristics, using findings-diagnosis links, automatically generating, from a plurality of possible diagnoses included within the knowledge database, a subset including a plurality of possible diagnoses consistent with the descriptive characteristics collected from the user; and using the subset of possible diagnoses, automatically reorganizing an information space of said image database for concurrent presentation of a plurality of images related to the plurality of possible diagnoses for user review via the user-interface.

4. The method of claim 3, wherein said diagnostic engine operates dynamically, using the subset of diagnoses, to reorganize the information space in response to the user's modification of at least one of the plurality of descriptive characteristics.

5. A computer system for reducing diagnostic uncertainty using cross-referenced knowledge and image databases, comprising:

a user-interface to solicit a plurality of characteristics of diagnoses from a user;

a diagnostic engine operating under the programmatic control of the computer system and having access to the knowledge database, the knowledge database including a plurality of findings-diagnosis links representing relationships between findings and diagnoses, wherein said characteristics of diagnoses are employed to automatically identify, from the diagnoses for which data is stored in the knowledge database, a subset including a plurality of possible diagnoses from the knowledge database that are consistent with the characteristics; and using the subset of possible diagnoses identified from the findings-diagnosis links, automatically reorganizing an information space of the image database for presentation to the user, including concurrent presentation of a plurality of images on said user-interface for user review, the plurality of images being representative of at least two possible diagnoses.

6. The system of claim 5, wherein the plurality of images are presented as a diagnostic image stack.

7. The system of claim 6, wherein the diagnostic image stack comprises:

a subset of said plurality of images, each image in said subset being associated with a common diagnosis; and an index into said subset of images wherein the index is independent of the common diagnosis.

8. The system of claim 6, wherein the diagnostic image stack is displayed to depict stages of disease progression.

9. The system of claim 6, wherein the diagnostic image stack is displayed to depict a plurality of images associated with a particular diagnosis.

10. The system of claim 5, wherein at least one image presented to the user includes a display of associated characteristics of diagnoses when a user selects a portion of an image being displayed.

11. The system of claim 5, wherein the presentation to the user is accomplished through a display, and where the display concurrently indicates textual information retrieved from the knowledgebase that is related to at least one of the subset of possible diagnoses.

12. The system of claim 5, wherein the diagnostic engine uses the characteristics of diagnoses to perform a pattern recognition operation on the knowledge database and to identify possible diagnoses with matching characteristics.

13. The system of claim 5, wherein the system for reducing diagnostic uncertainty is applicable to and includes characteristics of diseases that have a dermatological manifestation.

14. The system of claim 5, wherein the system for reducing diagnostic uncertainty is applicable to and includes characteristics of diseases that are of a visual findings type visible to the unaided human eye.

15. The system of claim 5, wherein the system for reducing diagnostic uncertainty is applicable to and includes characteristics of diseases that are determined based upon a finding determined by mechanical examination means.

16. The system of claim 5, wherein the user-interface to solicit a plurality of characteristics includes at least one symptom represented as an icon.

17. The system of claim 16, wherein the icon is an image depicting the form of a dermatological lesion.

18. The system of claim 16, wherein the icon is an image depicting a distribution of the dermatological lesions about a patient's body.

19. The system of claim 5, wherein the system for reducing diagnostic uncertainty is applicable to and includes characteristics of oral medications.

20. The system of claim 9, wherein the iconic representation is an image depicting the shape of an oral medication.

21. The system of claim 19, wherein the iconic representation is an image depicting a color of an oral medication.

22. The system of claim 5, wherein the system for reducing diagnostic uncertainty is applicable to and includes characteristics determined during an autopsy.

23. The system of claim 5, wherein the system for reducing diagnostic uncertainty is applicable to and includes characteristics of a crime scene.

24. The system of claim 5, wherein the plurality of characteristics of diagnoses are selected from the group consisting of:
   Travel History;
   Occupation;
   Exposures;
   Radiological Signs;
   Medications;
   Habits;
   Cutaneous Signs;
   Morphology;
   Dysmorphology;
   Cutaneous Morphology; and
   Distribution.

25. A method for controlling a computer to accomplish a diagnosis, comprising:
   creating an image database from a collection of images pertaining to a particular subject matter, the image database being accessible by the computer;
   crating a knowledge database including a plurality of findings-diagnosis links representing relationships between findings and diagnoses, said knowledge database including cross-references to said image database, for the purpose of assisting in the diagnostic process, the knowledge database also being accessible by the computer;
   receiving, through a user-interface adapted to the particular subject matter, a plurality of descriptive characteristics of a sample requiring diagnosis;
   the computer operating a diagnostic engine, responsive to said descriptive characteristics, the diagnostic engine using the findings-diagnosis links to automatically generate, from a plurality of possible diagnoses included within the knowledge database, a subset including a plurality of possible diagnoses consistent with the descriptive characteristics collected from the user; and
   automatically reorganizing an information space of said image database for concurrent display of a plurality of images related to the subset of possible diagnoses for user review via the user-interface.

26. The method according to claim 25, wherein receiving a plurality of descriptive characteristics includes visual findings.

27. The method according to claim 26, wherein said visual findings are entered through the user interface by selection of a picon.

28. The method according to claim 26, wherein said visual findings are entered through the user interface by selection of an image.

29. The method according to claim 25, wherein said knowledge database includes at least one diagnostic module, and where the available descriptive characteristics are defined in accordance with the diagnostic module.

30. The method according to claim 29, wherein said at least one diagnostic module includes diagnoses associated with the module based upon medical literature.

* * * * *